(12) United States Patent
Lansalot-Matras et al.

(10) Patent No.: US 8,436,115 B2
(45) Date of Patent: May 7, 2013

(54) CATALYST SYSTEMS BASED ON CARBONYLAMINO FULVENES

(75) Inventors: Clément Lansalot-Matras, Vezin-le-coquet (FR); Olivier Lavastre, Gahard (FR); Sabine Sirol, Horrues (BE)

(73) Assignees: Total Petrochemicals Research Feluy, Seneffe (Feluy) (BE); Centre National de la Recherche Scientifique (CNRS), Paris (FR)

( * ) Notice: Subject to any disclaimer, the term of this patent is extended or adjusted under 35 U.S.C. 154(b) by 432 days.

(21) Appl. No.: 12/670,204

(22) PCT Filed: Jul. 16, 2008

(86) PCT No.: PCT/EP2008/059282
§ 371 (c)(1),
(2), (4) Date: Aug. 23, 2010

(87) PCT Pub. No.: WO2009/013196
PCT Pub. Date: Jan. 29, 2009

(65) Prior Publication Data
US 2010/0311931 A1   Dec. 9, 2010

(30) Foreign Application Priority Data

Jul. 24, 2007   (EP) .................................. 07290931

(51) Int. Cl.
*C08F 4/69* (2006.01)
*C08F 4/78* (2006.01)
*C07F 11/00* (2006.01)

(52) U.S. Cl.
USPC ........... 526/172; 526/161; 526/348; 526/351; 526/352; 526/169; 526/169.1; 556/57; 556/136; 556/138

(58) Field of Classification Search .................... 556/57; 526/172, 161
See application file for complete search history.

(56) References Cited

FOREIGN PATENT DOCUMENTS
EP        1 997 834 A1 * 12/2008

OTHER PUBLICATIONS

Duda, L.; Erker, G.; Frohlich, R.; Zippel, F., Eur. J. Inorg. Chem., 1998, 1153-1162.*

* cited by examiner

Primary Examiner — Rip A. Lee

(57) ABSTRACT

The present invention discloses metallic complexes based on carbonylamino fulvene ligands; their method of preparation and their use in the oligomerisation or polymerisation of ethylene and alpha-olefins.

13 Claims, 3 Drawing Sheets

CATALYST SYSTEMS BASED ON CARBONYLAMINO FULVENES

CROSS-REFERENCE TO RELATED APPLICATIONS

This application claims the benefit of PCT/EP2008/059282, filed Jul. 16, 2008, which claims priority from EP 07290931.0, filed Jul. 24, 2007.

The present invention discloses catalyst components based on carbonylamino fulvene ligands their method of preparation and their use in the polymerisation of ethylene and alpha-olefins.

Several ligands have been described in literature, some of which were tested in complexation with metals but none of them have been used as catalysts for the polymerisation of ethylene or alpha-olefins. Some ligands are described for example in Lloyd and Preston (D. Lloyd, N. W. Preston, J. Chem. Soc. C, 1969, 2464-2469.) or by Linn and Sharkey (W. J. Linn, W. G. Sharkey J. Am. Chem. Soc. 1957, 79, 4970-2.) or in Snyder et al. (C. A. Snyder, J. P. Selegue, N. C. Tice, C. E. Wallace. M. T. Blankenbuehler, S. Parkin, K. D. E. Allen, R. T. Beck, J. Am. Chem. Soc. 2005, 127, 15010-11.) or in Dong et al. (Y. B. Dong, Y. Geng, J. P. Ma and R. Q. Huang, Inorg. Chem. 2005, 44, 1693-1703.)

There is a need to develop new catalyst system having good activity and able to produce polymers tailored to specific needs.

It is an aim of the present invention to prepare new catalyst components that can be used in the polymerisation of ethylene and alpha-olefins.

It is also an aim of the present invention to provide very active catalyst components.

It is another aim of the present invention to provide a method for polymerising or copolymerising ethylene and alpha-olefins.

The present invention reaches, at least partially, any one of those aims.

Accordingly, the present invention discloses a method for preparing a metallic complex that comprises the steps of:

a) preparing a carbonylamino fulvene ligand by condensation reaction of an hydroxycarbonyl fulvene ligand with a primary amine, in a polar solvent and with an acid catalyst

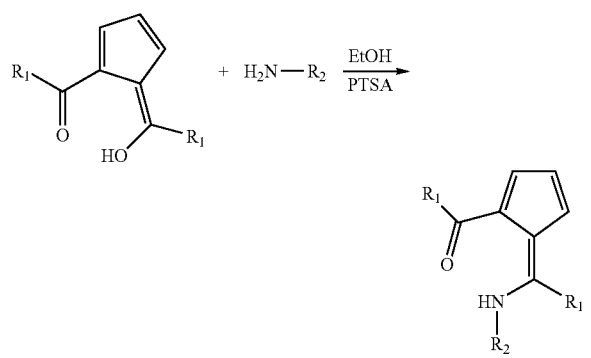

wherein $R_1$ and $R_2$ are the same or different and are selected from alkyl, aryl, alkylaryl, arylalkyl having at most 20 carbon atoms or heteroatoms-containing groups;

b) providing a metallic precursor $MZ_n$ wherein M is a metal Group 6 to 11 of the Periodic Table, Z is a negative counter-anion and n is the valence of M;

c) complexing the metallic precursor of step b) with the carbonylamino fulvene of step a);

d) retrieving a metallic complex.

Preferably, both $R_1$ are the same and are selected from alkyl, unsubstituted or substituted phenyl (Ph), CHPh2 wherein Ph may be substituted or not, or the $R_1$ groups include heteroatom(s)-containing units. More preferably R is $CHPh_2$ or cyclohexyl or paramethoxyphenyl. Most preferably $R_1$ is $CHPh_2$.

Preferably $R_2$ is $CH_2$pyridine or includes heteroatoms-containing units. More preferably $R_2$ is $CH_2$pyridine or furan.

Preferred embodiments according to the present invention are characterised by the following pairs:
Both $R_1$ are $CHPh_2$ and $R_2$ is $CH_2$pyridine,
Both $R_1$ are paramethoxyphenyl and $R_2$ is $CH_2$pyridine,
Both $R_1$ are cyclohexyl and $R_2$ is furan.
Most preferably, both $R_1$ are $CHPh_2$ and $R_2$ is $CH_2$pyridine.
Preferably, M is CrII, CrIII or Ni, more preferably, it is CrII.

Preferably Z is halogen or acetate, more preferably, it is Cl.

The preferred polar solvent is ethanol and the preferred acid catalyst is paratoluene sulfonic acid.

Several types of metallic complexes can be formed, one where the metal is coordinated to one ligand and one where the metal is coordinated to two ligands. The relative amounts of each ligand and metal unit depend upon the nature of ligand and of the metal. The amount of ligand must therefore be of at least one equivalent of ligand per metallic equivalent. In a preferred embodiment according to the present invention, the metal is CrII and it is coordinated to one ligand or two ligands.

The present invention further discloses an active catalyst system comprising the metallic complex and an activating agent having an ionising action.

Suitable activating agents are well known in the art. The activating agent can be an aluminium alkyl represented by formula $AlR^+{}_nX_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively and preferably, it is an aluminoxane and comprise oligomeric linear and/or cyclic alkyl aluminoxanes represented by formula

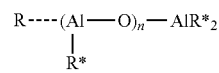

for oligomeric, linear aluminoxanes and by formula

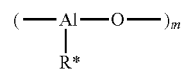

for oligomeric, cyclic aluminoxane,
wherein n is 1-40, preferably 10-20, m is 3-40, preferably 3-20 and R* is a $C_1$-$C_8$ alkyl group and preferably methyl.

The amount of activating is selected to give an Al/M ratio of from 100 to 3000, preferably of about 1000.

Suitable boron-containing activating agents may comprise a triphenylcarbenium boronate such as tetrakis-pentafluorophenyl-borato-triphenylcarbenium as described in EP-A-0427696, or those of the general formula [L'–H]+[B Ar$_1$ Ar$_2$ $X_3 X_4$]—as described in EP-A-0277004 (page 6, line 30 to page 7, line 7). The amount of boron-containing activating agent is selected to give B/M ratio of from 0.5 to 5, preferably of about 1.

The preferred activating agent is methylaluminoxane (MAO).

In another embodiment, according to the present invention, the metallic complex may be deposited on a conventional support impregnated with an activating agent.

Preferably, the conventional support is silica impregnated with methylaluminoxane (MAO). Alternatively, it can be an activating support such as fluorinated alumina silica.

The present invention further discloses a method for preparing an active catalyst system that comprises the steps of:
 a) providing a carbonylamino fulvene ligand;
 b) complexing the ligand of step a) with a metallic salt $MZ_n$ in a solvent with an acid catalyst;
 c) retrieving a catalyst component;
 d) optionally depositing the catalyst component of step c) on a support;
 e) activating the catalyst component of step c) or step d) with an activating agent having an ionising action;
 f) optionally adding a scavenger;
 g) retrieving an active oligomerisation or polymerisation catalyst system.

Alternatively, in step d), the catalyst component is deposited on a support impregnated with an activating agent or on an activating support. In that case, the activating step e) is not necessary.

The scavenger may be selected from triethylaluminium, triisobutylaluminum, tris-n-octylaluminium, tetraisobutyl-dialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
 a) injecting the active catalyst system into the reactor;
 b) injecting the monomer and optional comonomer;
 c) maintaining under polymerisation conditions;
 d) retrieving the oligomers and/or polymer.

The pressure in the reactor can vary from 0.5 to 60 bars, preferably from 15 to 45 bars. The productivity of the catalyst system increases with increasing pressure.

The polymerisation temperature can range from 10 to 100° C., preferably from 25 to 55° C. The productivity of the catalyst system decreases with increasing temperature.

Preferably the monomer and optional comonomer are selected from ethylene, propylene or 1-hexene.

The present invention also discloses the polymers obtained with the new catalyst systems.

LIST OF FIGURES

EXAMPLES

Synthesis of Ligands

The ligands were prepared following methods similar to those described for example in Lloyd and Preston (D. Lloyd, N. W. Preston, J. Chem. Soc. C, 2464-2469, 1969.)

All reactives were purchased from commercially available sources and used without purification and the solvents were purified following standard procedures. The NMR spectra were recorded either on a Brücker ARX 200 spectrometer, at 200 MHz for $^1H$ spectra and at 50 MHz for $^{13}C$ spectra, or on a Brücker AC 300P at 300 MHz for $^1H$ spectra and at 75 MHz for $^{13}C$ spectra. Mass spectras were obtained with a high resolution mass spectrometer Varian MAT 311 and microanalyses were carried out on a Flash EA1112 CHNS/O Thermo Electron (Centre Regional de Mesures des Physiques de l'Ouest, Rennes, France). Crystallographic data collection, unit cell constant and space group determination were carried out on an automatic 'Enraf Nonius FR590' NONIUS Kappa CCD diffractometer with graphite monochromatised Mo—Kα radiation at 120 K. The cell parameters are obtained with Denzo and Scalepack with 10 frames (psi rotation: 1° per frame). The structure was solved with SIR-97. The whole structure was refined with SHELXL97 by the full-matrix least-square techniques.

Parallel Synthesis of Carbonylamino Fulvene Ligands.

Carbonylamino fulvene ligands A, B, C, D, . . . U were synthesised in parallel with a Büchi Syncore. In each tube, 0.2 to 0.6 mmol of hydroxycarbonyl fulvene were introduced with 1.1 equivalents of amine, 0.5 mg of paratoluene-sulfonic acid (PTSA) and 20 ml of ethanol.

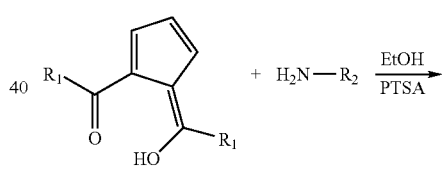

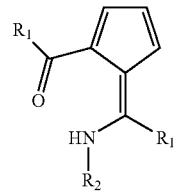

Figure 2:
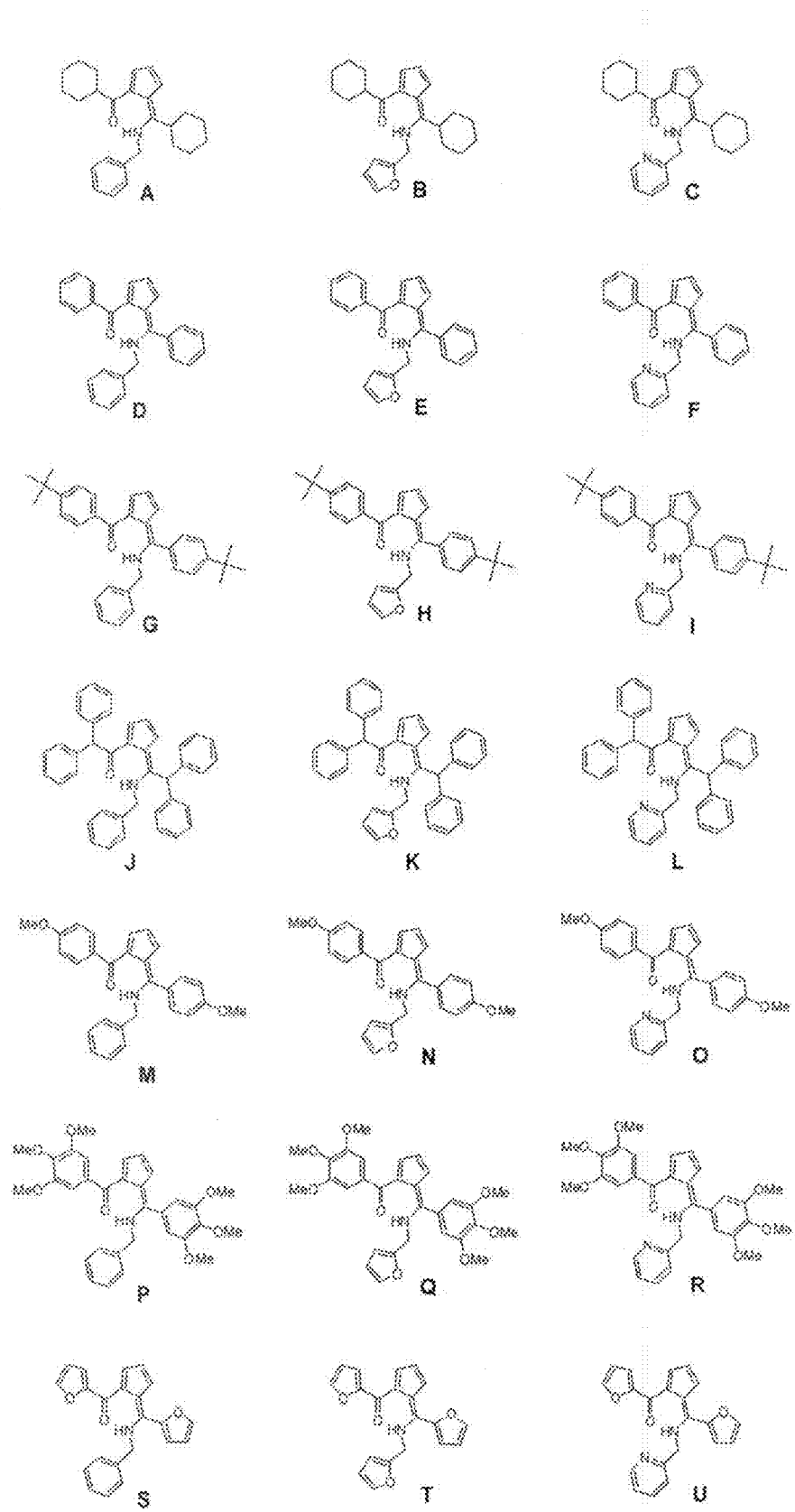
FIG. 2 represents examples of ligands prepared according to the present invention.

The mixtures were heated for a period of time of 12 h at a temperature of 80° C. Ligands A, B, C, J, K and L were heated for 12 additional hours at a temperature of 110° C. Ligands D and H were crystallised from ethanol. Otherwise, the solvent was evaporated under vacuum for 1 night and crude products were purified by column chromatography on silica gel and dried over $MgSO_4$ to afford new carbonylamino fulvene ligands. Several ligands synthetised according to the present invention are displayed in FIG. 2. The results for different amines are displayed in TABLE I for benzylamine; in TABLE II for furfurylamine and in TABLE III for picolylamine.

TABLE I

Synthesis with benzylamine.

| | R1= | 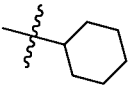 | 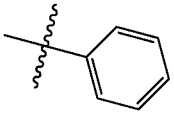 [SMILES: *c1ccccc1] | 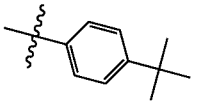 [SMILES: *c1ccc(C(C)(C)C)cc1] | 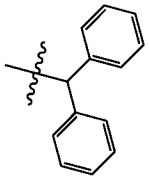 [SMILES: *C(c1ccccc1)c1ccccc1] |
|---|---|---|---|---|---|
| 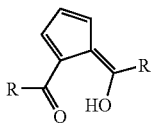 | $M_{hydroxycarbonylfulvene}$ (g/mol) | 286.41 | 274.31 | 386.53 | 454.56 |
| | $m_{hydroxycarbonylfulvene}$ (mg) | 165.6 | 168.2 | 218.5 | 109.7 |
| | $n_{hydroxycarbonylfulvene}$ (mmol) | 0.578 | 0.613 | 0.565 | 0.241 |
| 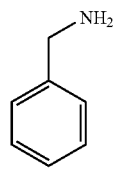 | $V_{amine}$ (µL) | 69 | 74 | 68 | 29 |
| | $n_{amine}$ (mmol) | 0.636 | 0.674 | 0.622 | 0.265 |
| | Purification | A<br>EtOAc/C7<br>1/1 | D<br>EtOAc/C7<br>1/1 | G<br>recristallisation<br>EtOH | J<br>DCM/C7<br>2/1 |
| 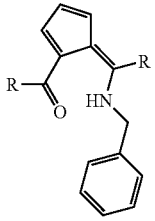 | $M_{carbonylaminofulvene}$ (g/mol) | 375.56 | 363.46 | 475.68 | 543.71 |
| | $m_{carbonylaminofulvene}$ (mg) | 144 | 200 | 230 | 68 |
| | $n_{carbonylaminofulvene}$ (mmol) | 0.383 | 0.550 | 0.484 | 0.125 |
| | Yield (%) | 66 | 90 | 86 | 52 |

| | R1= | 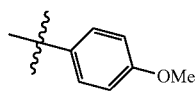 [SMILES: *c1ccc(OC)cc1] | 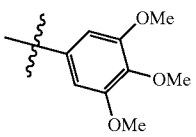 [SMILES: *c1cc(OC)c(OC)c(OC)c1] | 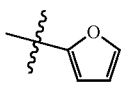 |
|---|---|---|---|---|
| 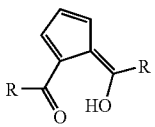 | $M_{hydroxycarbonylfulvene}$ (g/mol) | 334.37 | 454.16 | 254.24 |
| | $m_{hydroxycarbonylfulvene}$ (mg) | 200.0 | 167.6 | 105.1 |
| | $n_{hydroxycarbonylfulvene}$ (mmol) | 0.598 | 0.369 | 0.413 |
| 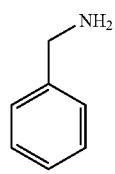 | $V_{amine}$ (µL) | 72 | 44 | 50 |
| | $n_{amine}$ (mmol) | 0.658 | 0.406 | 0.455 |
| | Purification | M<br>recristallisation<br>EtOH | P<br>EtOAc/C7<br>1/1 | S<br>EtOAc/C7<br>1/1 |

TABLE I-continued

Synthesis with benzylamine.

| | | | | |
|---|---|---|---|---|
| [structure: carbonylaminofulvene with benzyl group] | $M_{carbonylaminofulvene}$ (g/mol) | 423.52 | 543.31 | 343.39 |
| | $m_{carbonylaminofulvene}$ (mg) | 208 | 108 | 136 |
| | $n_{carbonylaminofulvene}$ (mmol) | 0.491 | 0.199 | 0.396 |
| | Yield (%) | 82 | 54 | 96 |

EtOAc = ethyl acetate, DCM = dichloromethane, C7 = heptane, EtOH = ethanol

TABLE II

Synthesis with furfurylamine

| | R1 = | cyclohexyl | phenyl | 4-tert-butylphenyl | diphenylmethyl |
|---|---|---|---|---|---|
| [hydroxycarbonylfulvene structure] | $M_{hydroxycarbonylfulvene}$ (g/mol) | 286.41 | 274.31 | 386.53 | 454.56 |
| | $m_{hydroxycarbonylfulvene}$ (mg) | 164.0 | 161.8 | 221.7 | 108.6 |
| | $n_{hydroxycarbonylfulvene}$ (mmol) | 0.573 | 0.590 | 0.574 | 0.239 |
| [furfurylamine structure] | $V_{amine}$ (µL) | 69 | 71 | 69 | 29 |
| | $n_{amine}$ (mmol) | 0.630 | 0.649 | 0.631 | 0.263 |
| | Purification | B EtOAc/C7 1/1 | E EtOAc/C7 1/1 | H EtOAc/C7 1/1 | K DCM/C7 2/1 |
| [carbonylaminofulvene structure] | $M_{carbonylaminofulvene}$ (g/mol) | 365.53 | 353.43 | 465.65 | 533.68 |
| | $m_{carbonylaminofulvene}$ (mg) | 178.0 | 195.0 | 206.0 | 93.0 |
| | $n_{carbonylaminofulvene}$ (mmol) | 0.487 | 0.552 | 0.442 | 0.174 |
| | Yield (%) | 85 | 94 | 77 | 73 |

| | R1 = | 4-methoxyphenyl | 3,4,5-trimethoxyphenyl | furyl |
|---|---|---|---|---|
| [hydroxycarbonylfulvene structure] | $M_{hydroxycarbonylfulvene}$ (g/mol) | 334.37 | 454.16 | 254.24 |
| | $m_{hydroxycarbonylfulvene}$ (mg) | 168.2 | 168.2 | 120.6 |
| | $n_{hydroxycarbonylfulvene}$ (mmol) | 0.503 | 0.370 | 0.474 |

TABLE II-continued

Synthesis with furfurylamine

| | | | | |
|---|---|---|---|---|
| $V_{amine}$ (µL) | | 49 | 44 | 57 |
| $n_{amine}$ (mmol) | | 0.553 | 0.407 | 0.522 |
| Purification | | N<br>EtOAc/C7<br>1/1 | Q<br>EtOAc/C7<br>1/1 | T<br>EtOAc/C7<br>1/1 |
| $M_{carbonylaminofulvene}$ (g/mol) | | 413.49 | 533.28 | 333.36 |
| $m_{carbonylaminofulvene}$ (mg) | | 76.0 | 108.0 | 153.0 |
| $n_{carbonylaminofulvene}$ (mmol) | | 0.183 | 0.203 | 0.459 |
| Yield (%) | | 36 | 55 | 97 |

EtOAc = ethyl acetate, DCM = dichloromethane, C7 = heptane, EtOH = ethanol

TABLE III

Synthesis with 2-picolylamine

| R1= | cyclohexyl | phenyl | 4-tert-butylphenyl | diphenylmethyl |
|---|---|---|---|---|
| $M_{hydroxycarbonylfulvene}$ (g/mol) | 286.41 | 274.31 | 386.53 | 454.56 |
| $m_{hydroxycarbonylfulvene}$ (mg) | 174.7 | 158.1 | 223.7 | 205.6 |
| $n_{hydroxycarbonylfulvene}$ (mmol) | 0.610 | 0.576 | 0.579 | 0.452 |
| $V_{amine}$ (µL) | 73 | 69 | 70 | 54 |
| $n_{amine}$ (mmol) | 0.671 | 0.634 | 0.637 | 0.498 |
| Purification | C<br>EtOAc/C7<br>1/1 | F<br>EtOAc/C7<br>1/1 | I<br>EtOAc/C7<br>1/1 | L<br>Ether/C7<br>1/1 |
| $M_{carbonylaminofulvene}$ (g/mol) | 376.55 | 364.45 | 476.67 | 544.70 |
| $m_{carbonylaminofulvene}$ (mg) | 187 | 193 | 187 | 174 |
| $n_{carbonylaminofulvene}$ (mmol) | 0.497 | 0.530 | 0.392 | 0.319 |
| Yield (%) | 81 | 92 | 68 | 71 |

TABLE III-continued

Synthesis with 2-picolylamine

| | | R1= | | | |
|---|---|---|---|---|---|
| | $M_{hydroxycarbonylfulvene}$ (g/mol) | | 334.37 | 454.16 | 254.24 |
| | $m_{hydroxycarbonylfulvene}$ (mg) | | 170.3 | 161.8 | 114.3 |
| | $n_{hydroxycarbonylfulvene}$ (mmol) | | 0.509 | 0.356 | 0.450 |
| | $V_{amine}$ (µL) | | 61 | 43 | 54 |
| | $n_{amine}$ (mmol) | | 0.560 | 0.392 | 0.495 |
| | Purification | | O EtOAc/C7 2/1 | R EtOAc/C7 2/1 | U EtOAc/C7 1/1 |
| | $M_{carbonylaminofulvene}$ (g/mol) | | 424.51 | 544.30 | 344.38 |
| | $m_{carbonylaminofulvenen}$ (mg) | | 129 | 109 | 93 |
| | $n_{carbonylaminofulvene}$ (mmol) | | 0.304 | 0.200 | 0.270 |
| | Yield (%) | | 60 | 56 | 60 |

EtOAc = ethyl acetate, DCM = dichloromethane, C7 = heptane, EtOH = ethanol

Ligand A: 1-(cyclohexanoyl)-6-benzylamino-6-cyclohexyl fulvene

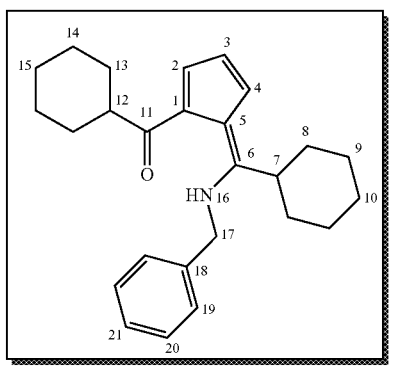

$C_{26}H_{33}NO$
Mol. Wt.: 375,54632
Pale green solid
Yield: 66%

$^1$H NMR (CDCl$_3$, 300 MHz, ppm) δ: 14.87 (1H, s, N$^{16}$H), 7.31 (2H, d, J=0.03 Hz, C$^2$H and C$^4$H), 7.21 (5H, m, C$^{19}$H, C$^{2O}$H and C$^{21}$H), 6.19 (1H, s, C$^3$H), 4.63 (2H, d, J=0.23 Hz, C$^{17}$H), 3.44-2.75 (2H, m, C$^{12}$H and C$^7$H), 1.83-0.97 (20H, m, C$^8$H, C$^9$H, C$^{10}$H, C$^{13}$H, C$^{14}$H, C$^{15}$H)

$^{13}$C NMR (CDCl$_3$, 50 MHz, ppm) δ: 199.23 (C$^{11}$), 173.58 (C$^6$), 137.93 (C$^{18}$), 131.82 (C$^2$), 130.60 (C$^4$), 128.84 (C$^{20}$), 127.67 (C$^{21}$), 127.14 (C$^{19}$), 123.97 (C$^1$), 117.01 (C$^5$), 116.03 (C$^3$), 47.87 (C$^{17}$), 47.04 (C$^{12}$), 42.03 (C$^{15}$), 32.26 (C$^8$), 31.06 (C$^{10}$), 26.99 (C$^{13}$), 26.32 (C$^{14}$), 26.21 (C$^9$), 25.85 (C$^7$).

HRMS: Calcd. for M+. (C$_{26}$H$_{33}$NO) m/z=375.25621. found 375.2571 (2 ppm).

Anal. Cacld for C$_{26}$H$_{33}$NO: C, 83.15; H, 8.86; N, 3.73, O, 4.26. found C, 82.71; H, 8.91; N, 4.00.

Ligand B: 1-(cyclohexanoyl)-6-(furan-2-yl methyl)amino-6-cyclohexyl fulvene

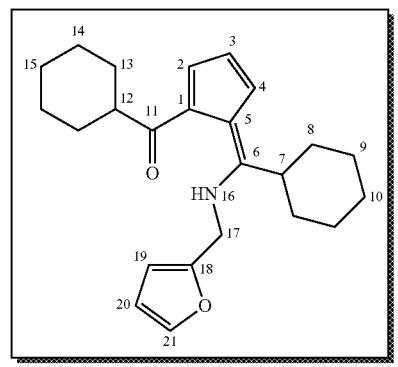

$C_{24}H_{31}NO_2$
Mol. Wt.: 365,51
Pale brown solid
Yield: 85%

¹H NMR (CDCl₃, 300 MHz, ppm) δ: 14.92 (1H, s, $N^{16}H$), 7.56 (1H, d, J=0.02 Hz, $C^{21}H$) 7.43 (2H, d, J=0.025 Hz, $C^2H$ and $C^4H$), 7.28 (1H, m, $C^{20}H$), 6.34-6.40 (2H, m, $C^3H$ and $C^{19}H$), 4.78 (2H, d, J=0.24 Hz, $C^{17}H$), 3.52-3.09 (2H, m, $C^{12}H$ and $C^7H$), 2.19-1.31 (20H, m, $C^8H$, $C^9H$, $C^{10}H$, $C^{13}H$, $C^{14}H$, $C^{15}H$–

¹³C NMR (CDCl₃, 50 MHz, ppm) δ: 199.11 ($C^{11}$), 173.22 ($C^6$), 150.40 ($C^{18}$), 142.43 ($C^{21}$), 132.02 ($C^2$), 130.83 ($C^4$), 124.01 ($C^1$), 117.06 ($C^5$), 116.12 ($C^3$), 110.68 ($C^{20}$), 107.90 ($C^{19}$), 46.93 ($C^7$), 41.74 ($C^{10}$), 40.95 ($C^{17}$), 32.44 ($C^{13}$), 30.98 ($C^{15}$), 27.00 ($C^8$), 26.28 ($C^9$), 26.17 ($C^{14}$), 25.87 ($C^{12}$).

HRMS: Calcd. for M+. ($C_{24}H_{31}NO_2$) m/z=365.23548. found 365.2344 (2 ppm).

Anal. Cald for $C_{24}H_{31}NO_2$: C, 78.86; H, 8.55; N, 3.83, O, 8.75. found C, 78.54; H, 8.60; N, 3.89.

Ligand C: 1-(cyclohexanoyl)-6-(pyridine-2-methyl) amino-6-cyclohexyl fulvene

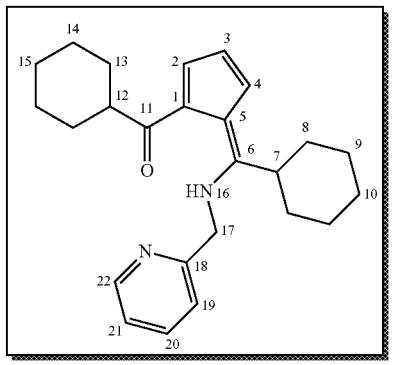

$C_{25}H_{32}N_2O$
Mol. Wt.: 376,53438
Pale brown solid
Yield: 81%

¹H NMR (CDCl₃, 300 MHz, ppm) δ: 15.01 (1H, s, $N^{16}H$), 8.59 (1H, d, J=0.01 Hz, $C^{22}H$), 7.68 (1H, t, J=0.025 Hz, $C^{20}H$), 7.45-7.51 (2H, m, $C^2H$ and $C^4H$), 7.36 (1H, s, $C^{19}H$), 7.22 (1H, t, J=0.02 Hz, $C^{21}H$), 6.34 (1H, t, J=0.02 Hz, $C^3H$), 4.92 (2H, d, J=0.26 Hz, $C^{17}H$), 3.60-2.95 (2H, m, $C^{12}H$ and $C_7H$), 1.96-1.31 (20H, m, $C^8H$, $C^9H$, $C^{10}H$–$C^{13}H$, $C^{14}H$, $C^{15}H$)

¹³C NMR (CDCl₃, 50 MHz, ppm) δ: 199.72 ($C^{11}$), 173.84 ($C^6$), 157.76 ($C^{18}$), 149.35 ($C^{22}$), 137.09 ($C^{19}$), 135.48 ($C^{20}$), 132.15 ($C^2$), 130.88 ($C^4$), 124.03 ($C^1$), 122.59 ($C^{21}$), 117.06 ($C^5$), 116.28 ($C^3$), 49.88 ($C^{17}$), 46.95 ($C^7$), 41.86 ($C^{10}$), 32.38 ($C^{13}$), 31.02 ($C^{15}$), 26.82 ($C^8$), 26.26 ($C^9$), 26.17 ($C^{14}$), 25.76 ($C^{12}$).

HRMS: Calcd. for M+. ($C_{25}H_{32}N_2O$) m/z=376.25146. found 376.2503 (3 ppm).

Anal. Cald for $C_{25}H_{32}N_2O$: C, 79.75; H, 8.57; N, 7.44, O, 4.25. found C, 79.34; H, 8.67; N, 7.27.

Ligand D: 1-benzoyl-6-benzylamino-6-phenyl fulvene

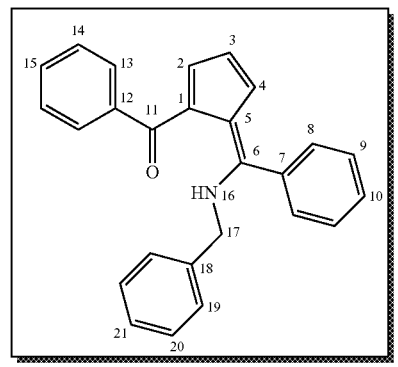

$C_{26}H_{21}NO$
Mol. Wt.: 363,45104
Brown solid
Yield: 90%

¹H NMR (CDCl₃, 300 MHz, ppm) δ: 15.28 (1H, s, $N^{16}H$), 7.51 (2H, m, $C^{13}H$), 7.20-6.88 (13H, m, $C^8H$, $C^9H$, $C^{10}H$, $C^{14}H$, $C^{15}H$, $C^{19}H$, $C^{20}H$, $C^{21}H$), 6.74 (1H, m, $C^2H$), 5.96 (1H, m, $C^4H$), 5.75 (1H, t, J=0.02 Hz, $C^3H$), 3.68 (2H, d, J=0.03 Hz, $C^{17}H$)

¹³C NMR (CDCl₃, 50 MHz, ppm) δ: 191.13 ($C_{11}$), 166.39 ($C^6$), 142.42 ($C^{12}$), 139.71 ($C^7$), 137.05 ($C^{18}$), 135.80 ($C^{15}$), 134.04 ($C^{10}$), 129.94 ($C^2$), 129.72 ($C^4$), 128.94 ($C^{20}$), 128.92 ($C^{13}$), 128.40 ($C^{14}$), 128.32 ($C^9$), 127.87 ($C^8$), 127.82 ($C^{21}$), 127.47 ($C^{19}$), 125.35 ($C^1$), 119.98 ($C^5$), 118.20 ($C^3$), 49.76 ($C^{17}$).

HRMS: Calcd. for M+. ($C_{26}H_{21}NO$) m/z=363.16231. found 363.1594 (1 ppm).

Anal. Cald for $C_{26}H_{21}NO$: C, 85.92; H, 5.82; N, 3.85, O, 4.40. found C, 85.46; H, 6.06; N, 3.99.

Cristallography. Single crystals of compound D suitable for a single crystal X-ray determination were obtained by evaporation of a saturated solution in THF.

| Empirical formula | C26 H21 N O |
|---|---|
| Formula weight | 363.44 |
| Temperature | 120(2) K |
| Wavelength | 0.71073 A |
| Crystal system, space group | Monoclinic, P 21/c |
| Unit cell dimensions | a = 6.22050(10) A alpha = 90 deg. |
| | b = 17.5271(3) A beta = 91.6710(10) deg. |
| | c = 18.2524(3) A gamma = 90 deg. |
| Volume | 1989.16(6) $A^3$ |
| Z, Calculated density | 4, 1.214 Mg/m³ |
| Absorption coefficient | 0.073 mm⁻¹ |
| F(000) | 768 |
| Crystal size | 0.2 × 0.15 × 0.1 mm |
| Theta range for data collection | 3.22 to 27.47 deg. |
| Limiting indices | −8 <= h <= 8, −22 <= k <= 22, −23 <= l <= 23 |
| Reflections collected/unique | 8885/4522 [R(int) = 0.0472] |
| Completeness to theta = | 27.47 99.3% |
| Absorption correction | none |

| | |
|---|---|
| Refinement method | Full-matrix least-squares on $F^2$ |
| Data/restraints/parameters | 4522/0/257 |
| Goodness-of-fit on $F^2$ | 1.078 |
| Final R indices [I > 2sigma(I)] | R1 = 0.0607, wR2 = 0.1598 |
| R indices (all data) | R1 = 0.0736, wR2 = 0.1702 |
| Extinction coefficient | 0.075(9) |
| Largest diff. peak and hole | 0.337 and −0.271 e.A$^{-3}$ |

Figure 1:
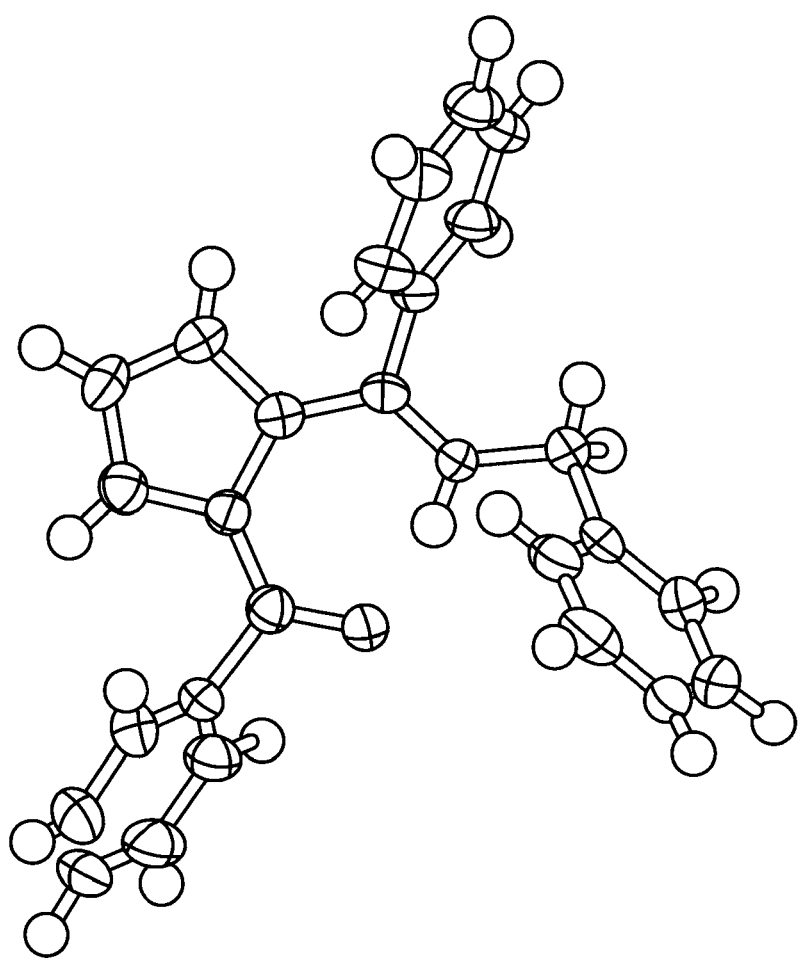
FIG. 1 represents the molecular structure of ligand D obtained by X-Ray.

The molecular structure of ligand D obtained by X-Ray is displayed in FIG. 1.

Ligand E: 1-benzoyl-6-(1-(furan-2-methyl)amino)-6-phenyl fulvene

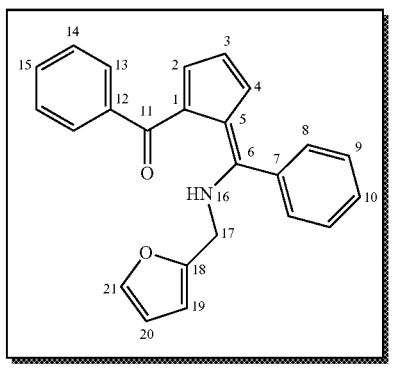

$C_{24}H_{19}NO_2$
Mol. Wt.: 353.41316
Red oil
Yield: 94%

$^1$H NMR (CDCl$_3$, 300 MHz, ppm) δ: 14.36 (1H, s, N$^{16}$H), 7.83 (2H, m, C$^{13}$H), 7.59-7.50 (8H, m, C$^8$H, C$^9$H, C$^{10}$H–C$^{14}$H, C$^{15}$H), 7.43 (1H, d, J=0.01 Hz, C$^2$H), 7.20 (1H, m, C$^{21}$H), 6.50 (1H, t, J=0.01 Hz, C$^{20}$H), 6.37 (1H, m, C$^4$H), 6.33-6.30 (2H, m, C$^3$H and C$^{19}$H), 4.49 (2H, d, J=0.02 Hz, C$^{17}$H)

$^{13}$C NMR (CDCl$_3$, 50 MHz, ppm) δ: 191.13 (C$^{11}$), 166.07 (C$^6$), 149.82 (C$^{18}$), 142.82 (C$^{21}$), 142.30 (C$^{12}$), 139.99 (C$^7$), 135.95 (C$^{15}$), 133.85 (C$^{10}$), 129.95 (C$^2$), 129.77 (C$^4$), 128.92 (C$^{13}$), 128.53 (C$^{14}$), 128.35 (C$^9$), 127.84 (C$^8$), 125.48 (C$^1$), 119.92 (C$^5$), 118.35 (C$^3$), 110.64 (C$^{20}$), 108.22 (C$^{19}$), 42.93 (C$^{17}$).

HRMS: Calcd. for M+. (C$_{24}$H$_{19}$NO$_2$) m/z=353.14158. found 353.1417 (0 ppm).

Anal. Cald for C$_{24}$H$_{19}$NO$_2$: C, 81.56; H, 5.42; N, 3.96, O, 9.05. found C, 80.35, H, 5.64; N, 4.13.

Ligand F: 1-benzoyl-6-(1-(pyridine-2-methyl)amino)-6-phenyl fulvene

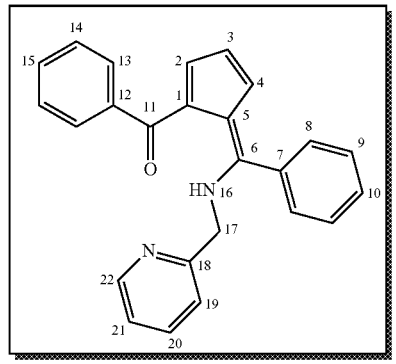

$C_{25}H_{20}N_2O$
Mol. Wt.: 364.4391
Brown solid
Yield: 92%

$^1$H NMR (CDCl$_3$, 300 MHz, ppm) δ: 14.49 (1H, s, N$^{16}$H), 8.56 (1H, d, J=0.01 Hz, C$^{22}$H), 7.80 (2H, m, C$^{13}$H), 7.70 (1H, t, J=0.025 Hz, C$^{20}$H), 7.54-7.42 (9H, m, C$^8$H, C$^9$H, C$^{10}$H, C$^{14}$H, C$^{15}$H, and C$^{19}$H), 7.22-7.17 (2H, m, C$^2$H, C$^{21}$H), 6.48 (1H, m, C$^4$H), 6.28 (1H, t, J=0.02 Hz, C$^3$H), 4.67 (2H, d, J=0.02 Hz, C$^{17}$H)

$^{13}$C NMR (CDCl$_3$, 50 MHz, ppm) δ: 191.14 (C$^{11}$), 166.69 (C$^6$), 156.79 (C$^{18}$), 149.59 (C$^{22}$), 142.27 (C$^7$), 139.99 (C$^{12}$), 137.13 (C$^{20}$), 136.02 (C$^{10}$), 133.89 (C$^{15}$), 129.95 (C$^2$), 129.72 (C$^4$), 128.92 (C$^{13}$), 128.31 (C$^{14}$), 128.30 (C$^9$), 127.81 (C$^8$), 125.50 (C$^5$), 122.60 (C$^{19}$), 121.31 (C$^{21}$), 119.97 (C$^1$), 118.33 (C$^3$), 51.41 (C$^{17}$).

HRMS: Calcd. for M+. (C$_{25}$H$_{20}$N$_2$O) m/z=364.15756. found 364.1557 (5 ppm).

Anal. Cald for: C, 82.39; H, 5.53; N, 7.69, O, 4.39. found C, 82.53; H, 5.56; N, 7.61.

Ligand G: 1-(4-tertbutylbenzoyl)-6-benzylamino-6-(4-tertbutylphenyl) fulvene

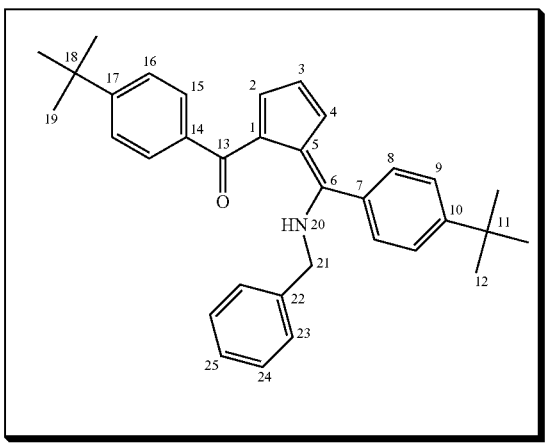

$C_{34}H_{37}NO$
Mol. Wt.: 475.66368
Yellow solid
Yield: 85%

$^1$H NMR (CDCl$_3$, 300 MHz, ppm) δ: 14.32 (1H, s, N$^{20}$H), 7.57 (2H, m, C$^{15}$H), 7.40-7.13 (11H, m, C$^8$H, C$^9$H, C$^{16}$H, C$^{23}$H–C$^{24}$H, C$^{25}$H), 6.34 (1H, m, C$^2$H), 6.11 (1H, m, C$^4$H), 5.17 (1H, t, J=0.02 Hz, C$^3$H), 4.38 (2H, d, J=0.02 Hz, C$^{21}$H), 1.30 (18H, d, J=0.03 Hz, C$^{12}$H$_3$ and C$^{19}$H$_3$).

$^{13}$C NMR (CDCl$_3$, 50 MHz, ppm) δ: 191.05 (C$^{13}$), 166.71 (C$^6$), 153.13 (C$^{17}$), 152.84 (C$^{10}$), 139.50 (C$^{14}$), 139.28 (C$^7$), 137.13 (C$^{22}$), 135.51 (C$^2$), 131.01 (C$^4$), 128.87 (C$^{24}$), 128.79 (C$^8$), 128.20 (C$^9$), 127.63 (C$^{16}$), 127.44 (C$^{16}$), 125.19 (C$^{25}$), 125.07 (C$^{23}$), 124.70 (C$^1$), 119.92 (C$^5$), 117.70 (C$^3$), 49.68 (C$^{21}$), 34.92 (C$^{11}$ and C$^{18}$), 31.35 (C$^{12}$ and C$^{19}$).

HRMS: Calcd. for M+. (C$_{34}$H$_{37}$NO) m/z=475.28752. found. 475.2899 (5 ppm)

Anal. Cald for C$_{34}$H$_{37}$NO: C, 85.85; H, 7.84; N, 2.94, O, 3.36. found C, 86.13; H, 7.99; N, 2.99.

Ligand H: 1-(4-tertbutylbenzoyl)-6-(1-(furan-2-methyl)amino)-6-(4-tertbutylphenyl) fulvene

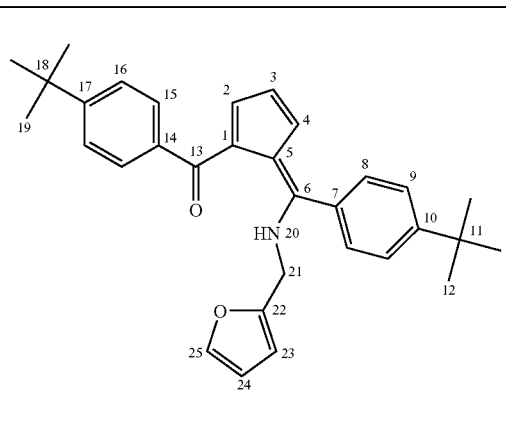

C$_{32}$H$_{35}$NO$_2$
Mol. Wt.: 465.6258
Yellow solid
Yield: 77%

$^1$H NMR (CDCl$_3$, 300 MHz, ppm) δ: 14.14 (1H, s, N$^{20}$H), 7.56 (2H, d, J=0.03 Hz, C$^{15}$H), 7.42-7.27 (6H, m, C$^8$H–C$^9$H, C$^{16}$H), 7.23 (1H, s, C$^2$H), 7.03 (1H, d', J=0.01 Hz, C$^{25}$H), 6.32 (1H, t, J=0.01 Hz, C$^{24}$H), 6.18-6.09 (1H, m, C$^3$H, C$^4$H and C$^{23}$H), 4.32 (2H, d, J=0.02 Hz, C$^{21}$H), 1.26 (18H, d, J=0.03 Hz, C$^{12}$H$_3$ and C$^{19}$H$_3$)

$^{13}$C NMR (CDCl$_3$, 50 MHz, ppm) δ: 191.09 (C$^{13}$), 166.41 (C$^6$), 153.17 (C$^{17}$), 152.91 (C$^{10}$), 149.98 (C$^{22}$), 142.66 (C$^{25}$), 139.62 (C$^{14}$), 139.46 (C$^7$), 135.72 (C$^2$), 130.88 (C$^4$), 128.93 (C$^8$), 128.38 (C$^9$), 125.39 (C$^{16}$), 125.15 (C$^{15}$), 124.71 (C$^1$), 119.93 (C$^5$), 117.92 (C$^3$), 110.58 (C$^{24}$), 108.08 (C$^{23}$), 42.99 (C$^{21}$), 34.88 (C$^{11}$ and C$^{18}$), 31.39 (C$^{12}$ and C$^{19}$).

HRMS: Calcd. for M+. (C$_{32}$H$_{35}$NO$_2$) m/z=465.26678. found 465.2669 (0 ppm).

Anal. Cald for C$_{32}$H$_{35}$NO$_2$: C, 82.54; H, 7.58; N, 3.01, O, 3.01. found C, 81.98; H, 7.57; N, 3.14.

Ligand I: 1-(4-tertbutylbenzoyl)-6-(1-(pyridine-2-methyl)amino)-6-(4-tertbutylphenyl) fulvene

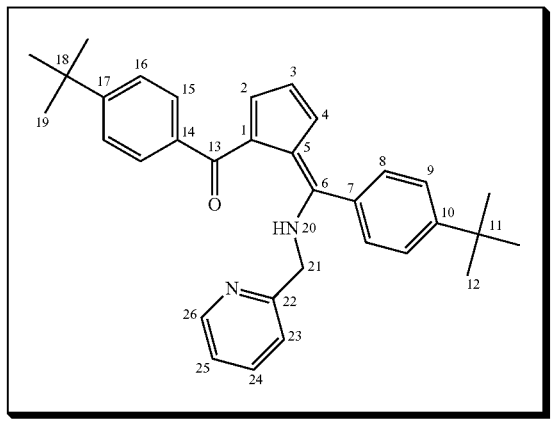

C$_{33}$H$_{36}$N$_2$O
Mol. Wt.: 476.65174
Yellow solid
Yield: 68%

$^1$H NMR (CDCl$_3$, 300 MHz, ppm) δ: 14.35 (1H, s, N$^{20}$H), 8.37 (1H, m, C$^{26}$H). 7.54 (2H, m, C$^{15}$H), 7.48 (1H, d, C$^{24}$H), 7.35-7.19 (7H, m, C$^8$H–C$^9$H, C$^{16}$H, C$^2$H), 7.05 (1H, m, C$^{23}$H), 7.01 (1H, t, J=0.02 Hz, C$^{25}$H), 6.34 (1H, m, C$^4$H), 6.11 (1H, t, J=0.02 Hz, C$^3$H), 4.52 (2H, d, J=0.02 Hz, C$^{21}$H), 1.24 (18H, s, C$^{12}$H$_3$ and C$^{19}$H$_3$)

$^{13}$C NMR (CDCl$_3$, 50 MHz, ppm) δ: 191.07 (C$^{13}$), 167.04 (C$^6$), 157.02 (C$^{26}$), 153.21 (C$^{17}$), 152.85 (C$^{10}$), 149.53 (C$^{24}$), 139.70 (C$^7$), 139.46 (C$^{14}$), 137.12 (C$^{23}$), 135.90 (C$^2$), 130.93 (C$^4$), 128.99 (C$^8$), 128.21 (C$^9$), 125.46 (C$^{16}$), 125.16 (C$^{15}$), 124.74 (C$^1$), 122.50 (C$^{22}$), 121.24 (C$^{25}$), 120.06 (C$^5$), 118.02 (C$^3$), 51.47 (C$^{21}$), 34.92 (C$^{11}$ and C$^{18}$), 31.39 (C$^{12}$ and C$^{19}$).

HRMS: Calcd. for M+. (C$_{33}$H$_{36}$N$_2$O) m/z=476.28276. found 476.2830 (0 ppm).

Anal. Cald for C$_{33}$H$_{36}$N$_2$O: C, 83.15; H, 7.61; N, 5.88, O, 3.36. found C, 82.65; H, 7.77; N, 5.81.

Ligand J: 1-(diphenylacetyl)-6-benzylamino-6-(diphenylmethyl)fulvene

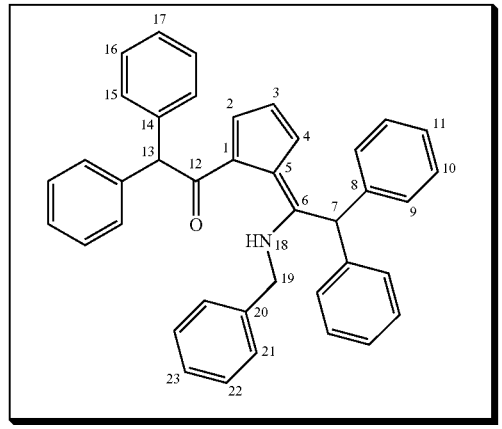

C$_{40}$H$_{33}$NO
Mol. Wt.: 543.69612
Yellow solid
Yield: 52%

$^1$H NMR (CDCl$_3$, 300 MHz, ppm) δ: 14.95 (1H, s, N$^{18}$H), 7.64 (1H, m, C$^2$H), 7.38-7.10 (25H, m, C$^9$H, C$^{10}$H–C$^{11}$H, C$^{15}$H, C$^{16}$H, C$^{17}$H, C$^{21}$H, C$^{22}$H and C$^{23}$H), 7.04 (1H, m, C$^4$H), 6.31 (1H, s, C$^{13}$H), 6.25-6.22 (2H, m, C$^3$H and C$^7$H,), 4.54 (2H, d, J=0.02 Hz, C$^{19}$H).

$^{13}$C NMR(CDCl$_3$, 50 MHz, ppm) δ: 193.03 (C$^{12}$), 167.51 (C$^6$), 141.30 (C$^{14}$), 138.85 (C$^8$), 136.42 (C$^{20}$), 134.93 (C$^2$), 133.10 (C$^4$), 129.27 (C$^{16}$), 128.95 (C$^{15}$), 128.92 (C$^{10}$), 128.58 (C$^{22}$), 128.39 (C$^9$), 127.31 (C$^{17}$), 126.96 (C$^{21}$), 126.65 (C$^{11}$), 125.92 (C$^1$), 120.39 (C$^5$), 117.60 (C$^3$), 58.95 (C$^{13}$), 52.10 (C$^{19}$), 49.46 (C$^7$).

HRMS: Calcd. for M+. (C$_{40}$H$_{33}$NO) m/z=543.25621. found 543.2539 (4 ppm).

Anal. Cald for C$_{40}$H$_{33}$NO: C, 88.36; H, 6.12; N, 2.58, O, 2.94. found C, 87.74; H, 6.07; N, 2.52.

Ligand K: 1-(diphenylacetyl)-6-(1-(furan-2-methyl)amino)-6-(diphenylmethyl) fulvene

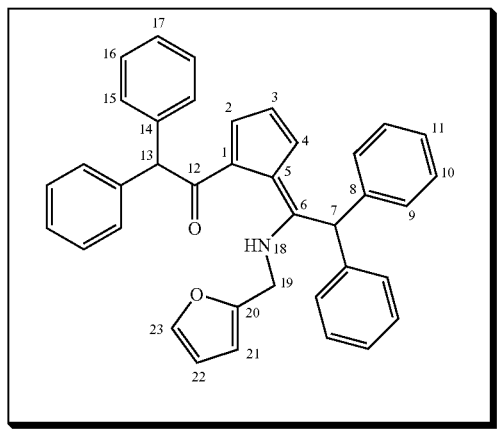

C$_{38}$H$_{31}$NO$_2$
Mol. Wt.: 533.65824
Yellow solid
Yield: 73%

$^1$H NMR (CDCl$_3$, 300 MHz, ppm) δ: 14.80 (1H, s, N$^{18}$H), 7.64 (1H, m, C$^2$H), 7.45-7.27 (21H, m, C$^9$H, C$^{10}$H, C$^{11}$H, C$^{15}$H, C$^{16}$H, C$^{17}$H and C$^{23}$H), 7.07 (1H, m, C$^4$H), 6.44 (1H, s, C$^{13}$H), 6.32 (1H, m, C$^{22}$H), 6.25 (1H, t, J=0.02 Hz, C$^3$H), 6.19 (1H, s, C$^{21}$H), 4.42 (2H, d, J=0.02 Hz, C$^{19}$H).

$^{13}$C NMR (CDCl$_3$, 50 MHz, ppm) δ: 192.99 (C$^{12}$), 167.02 (C$^6$), 149.35 (C$^{20}$), 142.34 (C$^{23}$), 141.27 (C$^{14}$), 138.66 (C$^8$), 135.22 (C$^2$), 133.07 (C$^4$), 129.27 (C$^{16}$), 128.99 (C$^{15}$), 128.93 (C$^{10}$), 128.36 (C$^9$), 127.36 (C$^{17}$), 126.62 (C$^{11}$), 126.01 (C$^1$), 120.29 (C$^5$), 117.74 (C$^3$), 110.52 (C$^{22}$), 107.87 (C$^{21}$), 58.94 (C$^{13}$), 52.10 (C$^{19}$), 43.26 (C$^7$).

HRMS: Calcd. for M+. (C$_{38}$H$_{31}$NO$_2$) m/z=533.23548. found 533.2349 (1 ppm).

Anal. Cald for C$_{38}$H$_{31}$NO$_2$: C, 85.52; H, 5.86; N, 2.62, O, 6.00. found C, 85.27; H, 5.95; N, 2.59.

Ligand L: 1-(diphenylacetyl)-6-(1-(pyridine-2-methyl)amino)-6-(diphenylmethyl) fulvene

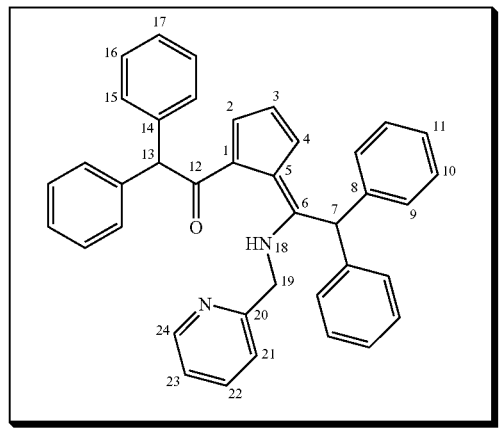

C$_{39}$H$_{32}$N$_2$O
Mol. Wt.: 544.68418
Brown solid
Yield: 70%

$^1$H NMR (CDCl$_3$, 300 MHz, ppm) δ: 14.94 (1H, t, J=0.02 Hz, N$^{18}$H,), 8.45 (1H, d, J=0.02 Hz C$^{24}$H), 7.68 (1H, m, C$^2$H), 7.50 (1H, t, J=0.03 Hz C$^{22}$H), 7.46-7.27 (21H, m, C$^9$H, C$^{10}$H, C$^{11}$H, C$^{15}$H, C$^{16}$H, C$^{17}$H, C$^{21}$H and C$^{23}$H), 7.09 (1H, m, C$^4$H), 6.39 (1H, s, C$^{13}$H), 6.27 (1H, t, J=0.02 Hz, C$^3$H), 6.25 (1H, s, C$^7$H), 4.76 (2H, d, J=0.02 Hz, C$^{19}$H).

$^{13}$C NMR (CDCl$_3$, 50 MHz, ppm) δ: 193.22 (C$^{12}$), 167.99 (C$^6$), 156.45 (C$^{24}$), 149.16 (C$^{22}$), 141.25 (C$^{14}$), 138.54 (C$^8$), 136.60 (C$^{21}$), 135.50 (C$^2$), 133.42 (C$^4$), 129.27 (C$^{16}$), 129.00 (C$^{15}$), 128.85 (C$^{10}$), 128.42 (C$^9$), 127.22 (C$^{17}$), 126.68 (C$^{11}$), 126.06 (C$^1$), 122.20 (C$^{22}$), 120.8 (C$^{25}$), 120.38 (C$^5$), 117.90 (C$^3$), (C$^{22}$), (C$^{21}$), 59.03 (C$^{13}$), 52.06 (C$^{19}$), 51.17 (C$^7$).

HRMS: Calcd. For M+. (C$_{39}$H$_{32}$N$_2$O) m/z=544.25146. found 544.2533 (3 ppm).

Anal. Cald for C$_{39}$H$_{32}$N$_2$O: C, 86.00; H, 5.92; N, 5.14, O, 2.94. found C, 86.08; H, 6.14; N, 4.80.

Ligand M: 1-(4-methoxybenzoyl)-6-(benzylamino)-6-(4-methoxyphenyl) fulvene

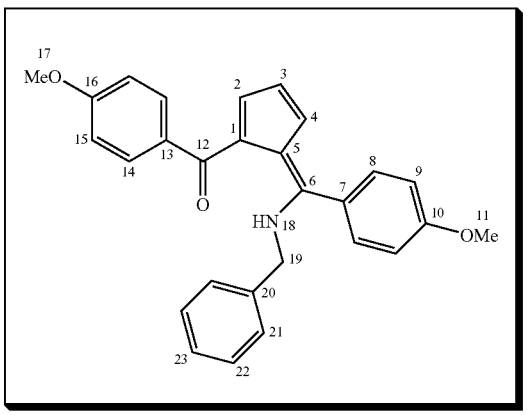

C$_{28}$H$_{25}$NO$_3$
Mol. Wt.: 423.503
Yellow solid
Yield: 82%

¹H NMR (CDCl₃, 300 MHz, ppm) δ: 14.26 (1H, s, N¹⁸H), 7.64 (2H, m, C¹⁴H), 7.22-7.12 (7H, m, C⁸H, C²¹H, C²²H and C²³H), 7.03 (1H, m, C²H), 6.90 (4H, m, C⁹H and C¹⁵H), 6.12 (1H, m, C⁴H), 3.77 (1H, t, J=0.02 Hz, C³H), 4.39 (2H, d, J=0.02 Hz, C¹⁹H), 3.78 (3H, s, C¹⁷H), 3.77 (3H, s, C¹¹H).

¹³C NMR (CDCl₃, 50 MHz, ppm) δ: 190.41 (C¹²), 166.52 (C⁶), 161.26 (C¹⁶), 160.56 (C¹⁰), 138.87 (C²⁰), 137.27 (C¹³), 135.20 (C²), 134.82 (C⁴), 131.06 (C¹⁵), 130.01 (C⁹), 128.81 (C²²), 127.61 (C²³), 127.28 (C²¹), 126.14 (C⁷), 125.19 (C¹), 120.09 (C⁵), 117.59 (C³), 113.56 (C¹⁴), 113.06 (C⁸), 55.42 (C¹⁷), 55.40 (C¹¹), 49.57 (C¹⁹).

HRMS: Calcd. for M+. (C₂₈H₂₅NO₃) m/z=423.18344. found 423.1821 (3 ppm).

Anal. Cald for C₂₈H₂₅NO₃: C, 79.41; H, 5.95; N, 3.31, O, 11.33. found C, 79.62; H, 5.95; N, 3.36.

Ligand N: 1-(4-methoxybenzoyl)-6-(1-(furan-2-methyl)amino)-6-(4methoxyphenyl) fulvene

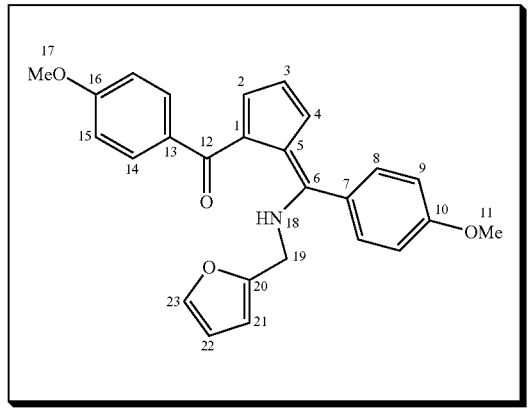

C₂₆H₂₃NO₄
Mol. Wt.: 413.46512
Yellow solid
Yield: 36%

¹H NMR (CDCl₃, 300 MHz, ppm) δ: 14.07 (1H, s, N¹⁸H), 7.63 (2H, d, J=0.04 Hz, C¹⁴H), 7.29 (2H, d, J=0.04 Hz, C⁸H), 7.27 (1H, m, C²³H), 7.03 (1H, m, C²H), 6.92 (2H, d, J=0.04 Hz, C¹⁵H), 6.83 (2H, d, J=0.04 Hz, C⁹H), 6.33 (1H, m, C⁴H), 6.22 (1H, m, C²²H), 6.15 (1H, d, J=0.01 Hz, C²¹H), 6.12 (1H, t, J=0.02 Hz, C³H), 4.35 (2H, D, J=0.02 Hz, C¹⁹H), 3.80 (3H, s, C¹⁷H), 3.78 (3H, s, C¹¹H).

¹³C NMR (CDCl₃, 50 MHz, ppm) δ: 190.41 (C¹²), 166.52 (C⁶), 161.26 (C¹⁶), 160.56 (C¹⁰), 142.64 (C²³), 139.15 (C²⁰), 137.27 (C¹³), 135.35 (C²), 134.82 (C⁴), 131.07 (C¹⁵), 130.17 (C⁹), 126.14 (C⁷), 125.19 (C¹), 120.09 (C⁵), 117.74 (C³), 113.60 (C¹⁴), 113.02 (C⁸), 110.51 (C²²), 107.96 (C²¹), 55.40 (C¹⁷ and C¹¹), 42.84 (C¹⁹).

HRMS: Calcd. for M+. (C₂₆H₂₃NO₄) m/z=413.16271. found 413.1614 (3 ppm)

Anal. Cald for: C, 75.53; H, 5.61; N, 3.39, O, 15.48. found C, 74.96; H, 5.59; N, 3.36.

Ligand O: 1-(4-methoxybenzoyl)-6-(1-(pyridine-2-methyl)amino)-6-(4-methoxyphenyl) fulvene

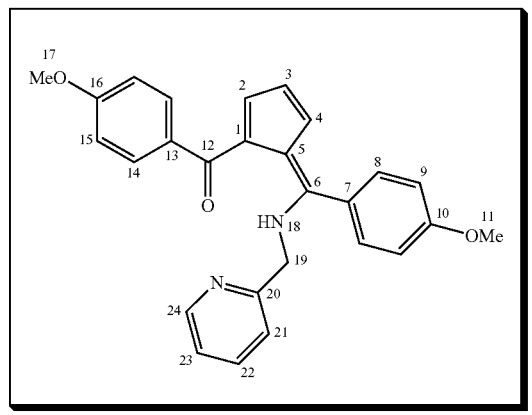

C₂₇H₂₄N₂O₃
Mol. Wt.: 424.49106
Yellow solid
Yield: 60%

¹H NMR (CDCl₃, 300 MHz, ppm) δ: 14.38 (1H, s, N¹⁸H), 8.53 (1H, d, J=0.01 Hz, C²⁴H), 7.80 (2H, d, J=0.03 Hz, C¹⁴H), 7.70 (1H, t, J=0.02 Hz, C²²H), 7.42 (1H, d, J=0.02 Hz, C²¹H), 7.33 (2H, d, J=0.02 Hz, C⁸H), 7.22-7.17 (2H, m, C²H and C²³H), 6.96 (4H, d, J=0.03 Hz, C¹⁵H and C⁹H), 6.47 (1H, m, C⁴H), 6.26 (1H, t, J=0.02 Hz, C³H), 4.67 (2H, d, J=0.03 Hz, C¹⁹H), 3.88 (3H, s, C¹⁷H), 3.87 (3H, s, C¹¹H).

¹³C NMR (CDCl₃, 50 MHz, ppm) δ: 190.46 (C¹²), 166.80 (C⁶), 161.35 (C¹⁶), 160.55 (C¹⁰), 156.90 (C²⁴), 149.01 (C²²), 139.34 (C²⁰), 137.61 (C¹³), 135.57 (C²), 134.68 (C⁴), 131.14 (C¹⁵), 130.01 (C⁹), 125.90 (C⁷), 125.44 (C¹), 122.65 (C²¹), 121.45 (C²³), 120.19 (C⁵), 117.92 (C³), 113.67 (C¹⁴), 113.08 (C⁸), 55.39 (C¹⁷ and C¹¹), 50.99 (C¹⁹).

HRMS: Calcd. for M+. (C₂₇H₂₄N₂O₃) m/z=424.17869. found 424.1775 (2 ppm).

Anal. Cald for C₂₇H₂₄N₂O₃: C, 76.39; H, 5.70; N, 6.60, O, 11.31. found C, 76.20; H, 5.73; N, 6.77.

Ligand P: 1-(3,4,5-trimethoxybenzoyl)-6-(benzylamino)-6-(3,4,5-trimethoxyphenyl) fulvene

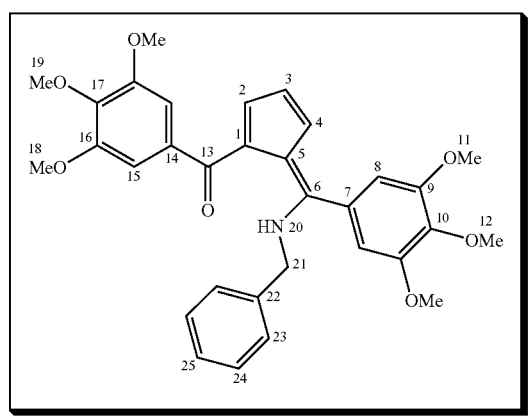

C₃₂H₃₃NO₇
Mol. Wt.: 543.60692
Yellow solid
Yield: 54%

$^1$H NMR (CDCl$_3$, 300 MHz, ppm) δ: 14.36 (1H, t, J=0.02 Hz, N$^{20}$H), 7.33-7.22 (6H, m, C$^2$H, C$^{23}$H, C$^{24}$H and C$^{25}$H), 7.03 (2H, s, C$^{15}$H), 6.57 (1H, m, C$^4$H), 6.51 (2H, s, C$^8$H), 6.27 (1H, t, J=0.01 Hz, C$^3$H), 4.50 (2H, d, J=0.02 Hz, C$^{21}$H), 3.92 (12H, s, C$^{11}$H and C$^{18}$H), 3.74 (6H, s, C$^{12}$H and C$^{19}$H).

$^{13}$C NMR (CDCl$_3$, 50 MHz, ppm) δ: 190.40 (C$^{13}$), 166.52 (C$^6$), 152.95 (C$^{16}$), 152.60 (C$^9$), 139.70 (C$^{17}$), 139.39 (C$^{10}$), 138.70 (C$^{14}$), 137.58 (C$^{22}$), 137.53 (C$^2$), 135.64 (C$^4$), 128.96 (C$^7$), 128.80 (C$^{24}$), 127.64 (C$^{23}$), 124.78 (C$^1$), 119.46 (C$^5$), 118.17 (C$^3$), 106.42 (C$^{15}$), 105.63 (C$^8$), 61.05 (C$^{19}$), 60.94 (C$^{12}$), 56.26 (C$^{18}$), 56.12 (C$^{11}$), 49.56 (C$^{21}$).

HRMS: Calcd. for M+. (C$_{32}$H$_{33}$NO$_7$) m/z=543.22570. found 543.2273 (2 ppm).

Anal. Cald for C$_{32}$H$_{33}$NO$_7$: C, 70.70; H, 6.12; N, 2.58, O, 20.60. found C, 70.93; H, 6.21; N, 2.61.

Ligand Q: 1-(3,4,5-trimethoxybenzoyl)-6-(1-(furan-2-methyl)amino)-6-(3,4,5-trimethoxy phenyl) fulvene

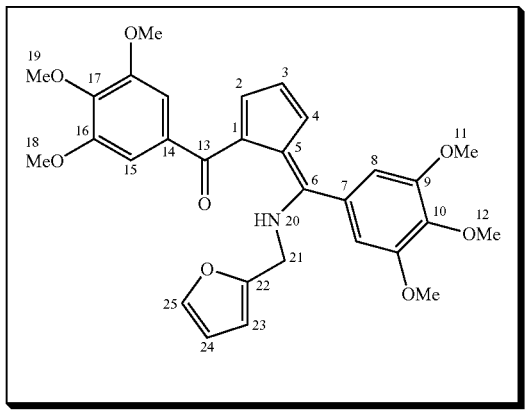

C$_{30}$H$_{31}$NO$_8$
Mol. Wt.: 533.56904
Yellow solid
Yield: 55%

$^1$H NMR (CDCl$_3$, 300 MHz, ppm) δ: 14.13 (1H, t, J=0.02 Hz, N$^{20}$H), 7.38 (1H, m, C$^{25}$H), 7.21 (1H, q, J=0.01 Hz, C$^2$H), 7.00 (1H, s, C$^{15}$H), 6.69 (1H, s, C$^8$H), 6.58 (1H, q, J=0.01 Hz, C$^4$H), 6.34 (1H, q, J=0.01 Hz, C$^{24}$H), 6.29-6.25 (2H, m, C$^3$H and C$^{23}$H), 4.47 (2H, d, J=0.02 Hz, C$^{21}$H), 3.96 (3H, s, C$^{19}$H), 3.92 (3H, s, C$^{12}$H), 3.91 (6H, s. C$^{18}$H), 3.87 (6H, s, C$^{11}$H).

$^{13}$C NMR (CDCl$_3$, 50 MHz, ppm) δ: 190.37 (C$^{13}$), 166.03 (C$^6$), 153.08 (C$^{16}$), 152.57 (C$^9$), 149.95 (C$^{25}$), 142.65 (C$^{22}$), 139.70 (C$^{17}$), 139.63 (C$^{10}$), 138.82 (C$^{14}$), 137.44 (C$^2$), 135.86 (C$^4$), 128.82 (C$^7$), 124.92 (C$^1$), 119.39 (C$^5$), 118.31 (C$^3$), 110.61 (C$^{22}$), 108.12 (C$^{15}$), 105.85 (C$^8$), 61.06 (C$^{19}$), 60.93 (C$^{12}$), 56.27 (C$^{18}$), 56.25 (C$^{11}$), 42.92 (C$^{21}$).

HRMS: Calcd. for M+. (C$_{30}$H$_{31}$NO$_8$) m/z=533.20497. found 533.2035 (2 ppm).

Anal. Cald for C$_{30}$H$_{31}$NO$_8$: C, 67.53; H, 5.86; N, 2.63, O, 23.99. found C, 67.82. H, 5.99; N, 4.94.

Ligand R: 1-(3,4,5-trimethoxybenzoyl)-6-(1-(Pyridine-2-methyl)amino)-6-(3,4,5-trimethoxyphenyl) fulvene

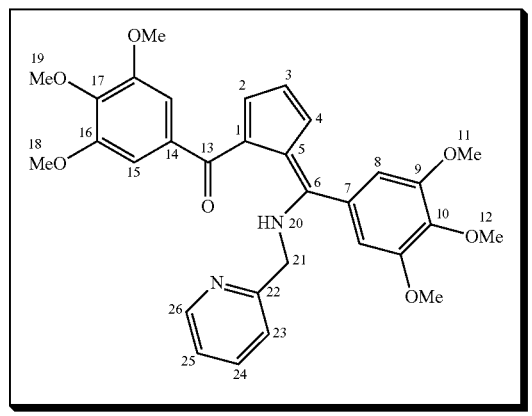

C$_{31}$H$_{32}$N$_2$O$_7$
Mol. Wt.: 544.59498
Yellow solid
Yield: 56%

$^1$H NMR (CDCl$_3$, 300 MHz, ppm) δ: 14.30 (1H, t, J=0.02 Hz, N$^{20}$H–, 8.55 (1H, d, J=0.01 Hz, C$^{26}$H), 7.70 (1H, t, J=0.02 Hz, C$^{24}$H), 7.38 (1H, d, J=0.03 Hz, C$^{23}$H), 7.24-7.18 (2H, m, C$^2$H and C$^{25}$H), 7.02 (1H, s, C$^{15}$H), 6.62 (1H, s, C$^8$H), 6.58 (1H, q, J=0.02 Hz, C$^4$H), 6.27 (1H, t, J=0.01 Hz, C$^3$H), 4.65 (2H, d, J=0.02 Hz, C$^{21}$H), 3.92 (12H, s, C$^{11}$H and C$^{18}$H), 3.75 (6H, s, C$^{12}$H and C$^{19}$H).

$^{13}$C NMR (CDCl$_3$, 50 MHz, ppm) δ: 190.38 (C$^{13}$), 166.68 (C$^6$), 157.03 (C$^{26}$), 152.98 (C$^{16}$), 152.56 (C$^9$), 149.60 (C$^{25}$), 139.62 (C$^{17}$ and C$^{10}$), 138.82 (C$^{14}$), 137.46 (C$^2$), 137.01 (C$^{22}$), 135.94 (C$^4$), 128.89 (C$^7$), 124.96 (C$^1$), 122.58 (C$^{25}$), 121.36 (C$^{23}$), 119.50 (C$^5$), 118.31 (C$^3$), 106.48 (C$^{15}$), 105.80 (C$^8$), 61.01 (C$^{19}$), 60.93 (C$^{12}$), 56.24 (C$^{18}$), 56.15 (C$^{11}$), 51.27 (C$^{21}$).

HRMS: Calcd. for M+. (C$_{31}$H$_{32}$N$_2$O$_7$) m/z=544.22095. found 544.2181 (5 ppm).

Anal. Cald for C$_{31}$H$_{32}$N$_2$O$_7$: C, 68.37; H, 5.92; N, 5.14, O, 20.56. found C, 68.16; H, 6.02; N, 4.96.

Ligand S: 1-furanoyl-6-benzylamino-6-furanyl fulvene

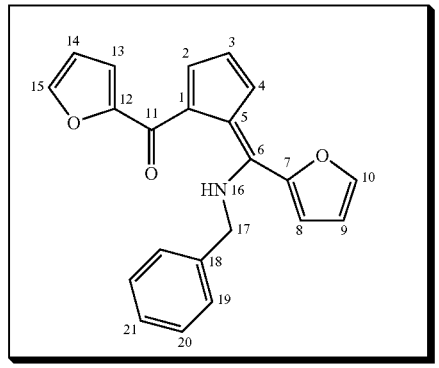

C$_{22}$H$_{17}$NO$_3$
Mol. Wt.: 343.38
Red solid
Yield: 96%

¹H NMR (CDCl₃, 300 MHz, ppm) δ: 13.90 (1H, s, N¹⁶H), 7.80 (1H, q, J=0.01 Hz, C¹⁵H), 7.68-7.67 (2H, m, C¹⁰H and C¹³H), 7.35-7.21 (5H, m, C¹⁹H, C²⁰H and C²¹H). 7.20 (1H, m, C²H), 6.92 (1H, q, J=0.01 Hz, C¹⁴H), 6.76 (1H, d, J=0.01 Hz, C⁸H), 6.59-6.57 (2H, m, C⁴H and C⁹H), 6.39 (1H, t, J=0.01 Hz, C³H), 4.65 (2H, d, J=0.02 Hz, C¹⁷H)

¹³C NMR (CDCl₃, 50 MHz, ppm) δ: 176.37 (C¹¹), 154.33 (C⁷), 153.95 (C¹²), 146.13 (C⁶), 145.32 (C¹⁵), 144.65 (C¹⁰), 137.64 (C²), 137.07 (C¹⁸), 134.91 (C⁴), 128.73 (C²⁰), 127.69 (C²¹), 127.44 (C¹⁹), 124.71 (C¹), 119.88 (C⁵), 118.83 (C³), 117.55 (C¹³), 117.34 (C¹⁴), 11.60 (C⁸), 111.45 (C⁹), 50.03 (C¹⁷).

HRMS: Calcd. for M+. (C₂₂H₁₇NO₃) m/z=343.12084. found 343.1210 (0 ppm).

Anal. Cald for C₂₂H₁₇NO₃: C, 76.95; H, 4.99; N, 4.08, O, 13.98. found C, 76.75; H, 5.15; N, 3.95.

Ligand T: 1-(furanoyl)-6-(1-(furan-2-methyl)amino)-6-(furanyl) fulvene

Ligand U: 1-(furanoyl)-6-(1-(pyridine-2-methyl)amino)-6-(furanyl) fulvene

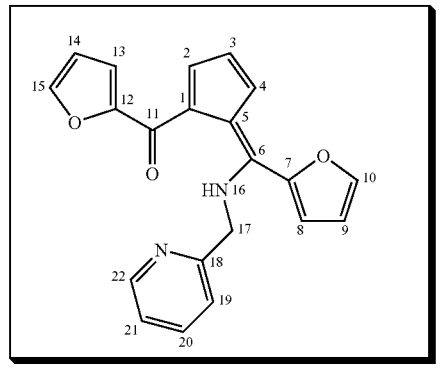

C₂₁H₁₆N₂O₃
Mol. Wt.: 344.36
Red solid
Yield: 60%

¹H NMR (CDCl₃, 300 MHz, ppm) δ: 13.90 (1H, s, N¹⁶H), 8.54 (1H, d, J=0.02 Hz. C²²H), 7.80 (1H, q, J=0.01 Hz, C¹⁵H), 7.70-7.60 (3H, m, C¹⁰H, C¹³H and C²⁴H), 7.42 (1H, d, J=0.03 Hz, C¹⁹H), 7.21-7.17 (2H, m, C²¹H and C²H), 6.92 (1H, q, J=0.01 Hz, C¹⁴H), 6.79 (1H, d, J=0.01 Hz, C⁸H), 6.57-6.54 (2H, m, C⁴H and C⁹H), 6.38 (1H, t, J=0.01 Hz, C³H), 4.78 (2H, d, J=0.02 Hz, C¹⁷H).

¹³C NMR (CDCl₃, 50 MHz, ppm) δ: 176.40 (C¹¹), 157.15 (C²²), 154.59 (C⁷), 153.92 (C¹²), 149.35 (C²⁰), 145.94 (C⁶), 145.35 (C¹⁵), 144.92 (C¹⁰), 137.98 (C²), 137.01 (C¹⁸), 135.15 (C⁴), 124.88 (C¹), 122.45 (C¹⁹), 121.25 (C²¹), 119.87 (C⁵), 119.07 (C³), 117.63 (C¹³) 117.59 (C¹⁴), 111.61 (C⁸), 111.37 (C⁹), 51.77 (C¹⁷).

HRMS: Calcd. for M+. (C₂₁H₁₆N₂O₃) m/z=344.11609. found 344.1155 (1 ppm).

Anal. Cald for C₂₁H₁₆N₂O₃: C, 73.24; H, 4.68; N, 8.13, O, 13.94. found C, 72.77; H, 4.73; N, 7.76.

Preparation of Metallic Complexes from Carbonylaminofulvenes

CrCl₃/Ligand A Complex.

7.51 mg (20 μmol) of ligand A and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

CrCl₂/Ligand A Complex.

7.51 mg (20 μmol) of ligand A and 1.23 mg (10 μmol) of CrCl₂ were introduced in a Schlenk with 100 μL of THF. The mixture was placed under stirring for 2 h at room temperature. The solvent was evaporated under vacuum overnight to yield a yellow brown solid.

CrCl₃/Ligand D Complex.

7.27 mg (20 μmol) of ligand D and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

¹H NMR (CDCl₃, 300 MHz, ppm) δ: 13.76 (1H, s, N¹⁶H), 7.79 (1H, q, J=0.01 Hz, C¹⁵H), 7.70 (1H, m, C¹⁰H), 7.66 (1H, m, C¹³H), 7.36 (1H, m, C¹⁹H), 7.19 (1H, d, J=0.01 Hz, C²H), 6.91 (1H, q, J=0.01 Hz, C¹⁴H), 6.84 (1H, d, J=0.01 Hz, C²¹H), 6.62 (1H, q, J=0.01 Hz, C²⁰H), 6.56 (1H, q, J=0.01 Hz, C⁴H), 6.38 (1H, t, J=0.01 Hz, C³H), 6.31 (1H, m, C⁸H), 6.27 (1H, m, C⁹H), 4.62 (2H, d, J=0.02 Hz, C¹⁷H)

¹³C NMR (CDCl₃, 50 MHz, ppm) δ: 176.36 (C¹¹), 153.93 (C⁷), 153.85 (C¹²), 149.92 (C²¹), 146.01 (C⁶), 145.32 (C¹⁵), 144.80 (C¹⁰), 142.61 (C¹⁸), 137.94 (C²), 134.98 (C⁴), 124.84 (C¹), 119.83 (C⁵), 119.82 (C³), 117.59 (C¹³ and C¹⁴), 111.60 (C⁸), 111.52 (C⁹), 110.52 (C²⁰), 108.02 (C¹⁹), 43.07 (C¹⁷).

HRMS: Calcd. for M+. (C₂₀H₁₅NO₄) m/z=333.10011. found 333.1008 (2 ppm).

Anal. Cald for C₂₀H₁₅NO₄: C, 72.06; H, 4.54; N, 4.20, O, 19.20. found C, 72.11; H, 4.55; N, 4.18.

CrCl₃/Ligand H Complex.

9.31 mg (20 μmol) of ligand H and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

CrCl₃/Ligand E Complex.

7.07 mg (20 μmol) of ligand E and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a red brown solid.

CrCl₃/Ligand C Complex.

7.53 mg (20 μmol) of ligand C and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

CrCl₃/Ligand B Complex.

7.31 mg (20 μmol) of ligand B and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

CrCl₃/Ligand O Complex.

8.49 mg (20 μmol) of ligand O and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

CrCl₃/Ligand L Complex.

10.89 mg (20 μmol) of ligand L and 3.75 mg (10 μmol) of CrCl₃.3THF were introduced in a Schlenk with 100 μL of tetrahydrofuran (THF). The mixture was placed under stirring for 2 h at room temperature. The solvent was evaporated under vacuum overnight to yield a yellow brown solid.

CrCl₂/Ligand L Complex.

10.89 mg (20 μmol) of ligand L and 1.23 (10 μmol) of CrCl₂ were introduced in a Schlenk with 100 μL of THF. The mixture was placed under stirring for 2 h at room temperature. The solvent was evaporated under vacuum overnight to yield a yellow brown solid.

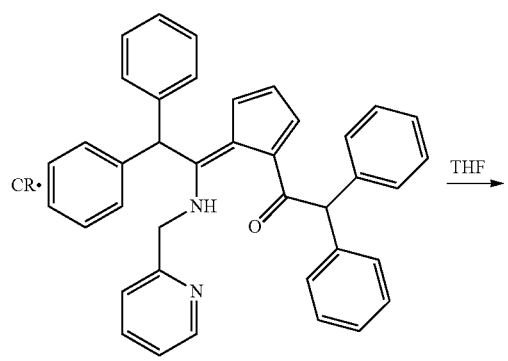

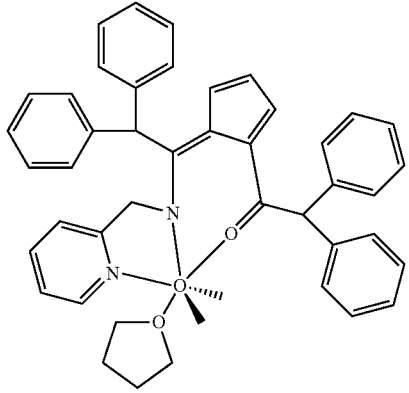

Figure 3:
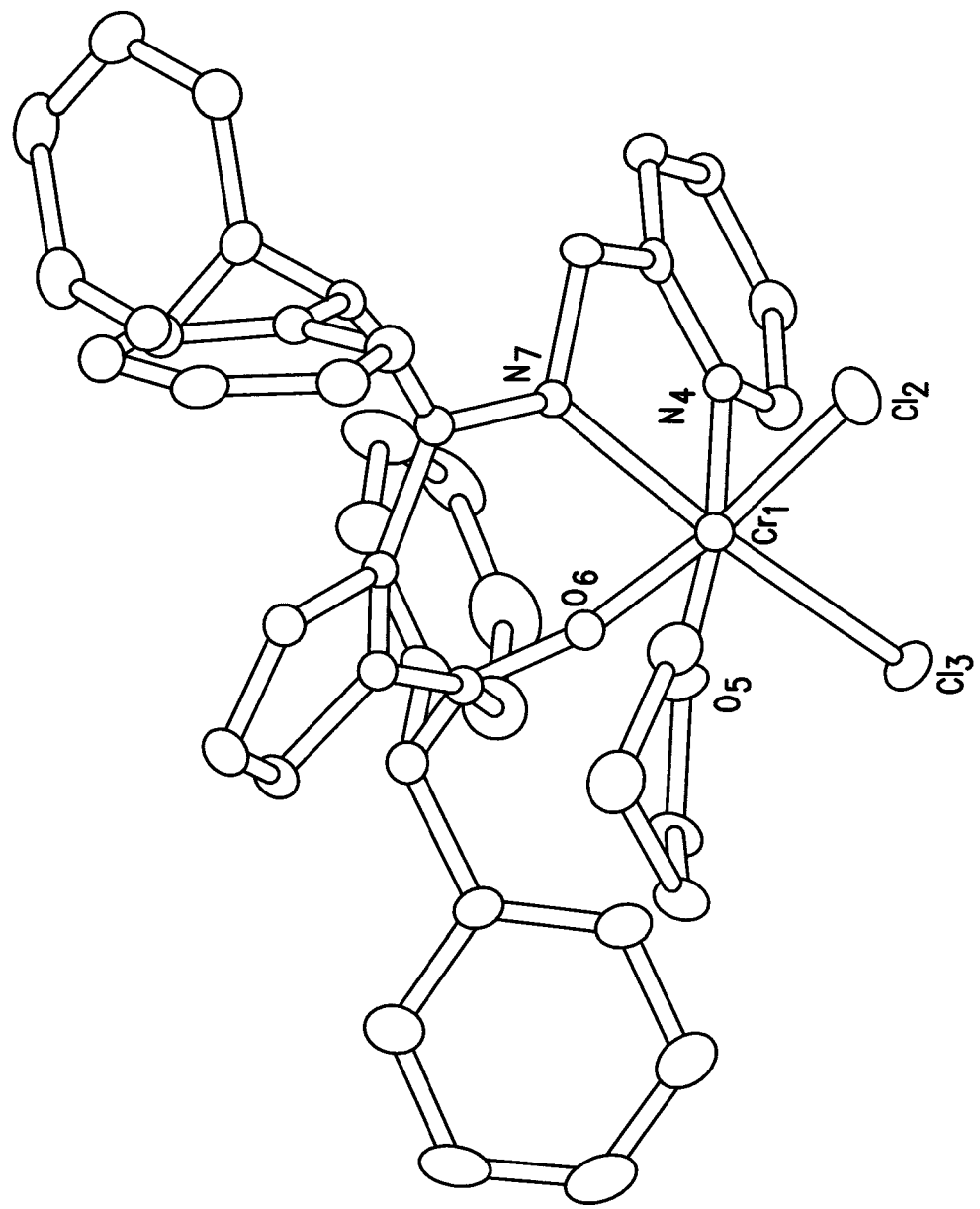
FIG. 3 represents the molecular structure of the metallic compound resulting from the complexation of $CrCl_2$ with ligand L.

The complex was recrystallised by slow diffusion of pentane in a saturated solution of the complex in THF. The crytals obtained were suitable for X-Ray analysis. The complex crystallises in a monoclinic environment with space group P 21/c. The chromium atom is coordinated by one molecule of tridentate fulvene by its oxygen atom and its two nitrogen atoms. The chromium atom is further coordinated by two chlorine atom and a THF molecule. This can be seen in FIG. 3. The complex is characterised as follows.

| | |
|---|---|
| Empirical formula | C43 H39 Cl2 Cr N2 O2 |
| Formula weight | 738.66 |
| Temperature | 100(2) K |
| Wavelength | 0.71073 A |
| Crystal system, space group | Monoclinic, P 21/c |
| Unit cell dimensions | a = 14.987(2) A alpha = 90 deg. |
| | b = 14.175(2) A beta = 99.485(9) deg. |
| | c = 17.412(3) A gamma = 90 deg. |
| Volume | 3648.4(9) A^3 |
| Z, Calculated density | 4, 1.345 Mg/m^3 |
| Absorption coefficient | 0.500 mm −1 |
| F(000) | 1540 |
| Crystal size | 0.2 × 0.2 × 0.03 mm |
| Theta range for data collection | 2.92 to 27.48 deg. |
| Limiting indices | −19 <= h <= 19, −18 <= k <= 11, −22 <= l <= 22 |
| Reflections collected/unique | 38703/8296 [R(int) = 0.0659] |
| Completeness to theta = | 27.48 99.2% |
| Absorption correction | Semi-empirical from equivalents |
| Max. and min. transmission | 0.985 and 0.885 |
| Refinement method | Full-matrix least-squares on F^2 |
| Data/restraints/parameters | 8296/0/451 |
| Goodness-of-fit on F^2 | 1.030 |
| Final R indices [I > 2sigma(I)] | R1 = 0.0423, wR2 = 0.0840 |
| R indices (all data) | R1 = 0.0728, wR2 = 0.0941 |
| Largest diff. peak and hole | 0.331 and −0.492 e.A^−3 |

Homogeneous polymerisation of ethylene.

The metallic catalyst component were activated with 1.625 mL of methylaluminoxane (MAO). The solution was stirred for 5 minutes and then diluted with 3.375 mL of toluene. The reactor was dried under nitrogen at a temperature of 90° C. for a period of time of 30 minutes. The reactor was brought to a polymerisation temperature of 35° C. and 50 mL of toluene were added to the reactor under nitrogen. A scavenger solution consisting of 0.5 mL of MAO (30%) and 4.5 mL of toluene was added to the reactor and the solution was stirred for a few minutes. The solution of activated catalyst was added to the reactor under nitrogen. The flux of nitrogen was interrupted, the reactor was purged and placed under an ethylene pressure of 15 bars. It was placed under stirring for a period of time of 1 h. The reactor was purged and the polymerisation was stopped by adding a 10% solution of MeOH/HCl. The polymer was washed 3 times with 30 mL of MeOH and 3 times with 30 mL of acetone. The polymer was dried under vacuum overnight at room temperature. The results are summarised in Table IV for the chromium-based catalyst systems.

TABLE IV

| M/L | m PE (g) | Activity ($kg_{PE}/(mol \cdot h)$) | Mn | Tm (° C.) |
|---|---|---|---|---|
| $CrCl_3$/A | 0.941 | 94.1 | — | 137 |
| $CrCl_2$/A | 0.976 | 97.6 | insoluble | 137 |
| $CrCl_3$/D | 0.995 | 99.5 | unfilterable | 119 |
| $CrCl_3$/H | 1.045 | 104.5 | unfilterable | 135 |
| $CrCl_3$/E | 1.244 | 124.4 | insoluble | 129 |
| $CrCl_3$/C | 1.283 | 128.3 | unfilterable | 135 |
| $CrCl_3$/B | 2.895 | 289.5 | unfilterable | 133 |
| $CrCl_3$/O | 3.648 | 364.8 | insoluble | 136 |
| $CrCl_3$/L | 5.415 | 541.5 | insoluble | 135 |
| $CrCl_2$/L | 6.915 | 691.5 | insoluble | 136 |

For all polymerisations, the conditions were as follows: Cr 10 μmol, ligand 20 μmol, polymerisation temperature 35° C., ethylene pressure 15 bars, 1000 eq. MAO, solvent: toluene, polymerisation time 1 h.

The highest activities were obtained with the catalyst systems based on $CrCl_3$/ligand L and $CrCl_2$/ligand L. As depicted in Table V, $CrCl_2$ based system is a selective catalyst whereas $CrCl_3$ based system is a mixed polymer/oligomer catalyst.

TABLE V

| M/L | m PE (g) | Activity ($kg_{PE}/(mol \cdot h)$) | Consumption ($kg_{C2H4}/(mol \cdot h)$) |
|---|---|---|---|
| $CrCl_2$/L | 4.11 | 411 | 385 |
| $CrCl_3$/L | 3.38 | 338 | 590 |

For all polymerisations, the conditions were as follows: Cr 10 μmol, ligand 20 μmol, polymerisation temperature 35° C., ethylene pressure 15 bars, 1000 eq. MAO, solvent: toluene, polymerisation time 1 h.

The activity of the system $CrCl_2$/ligand L has been studied as a function of temperature and of ethylene pressure. The results are displayed in Table VI. It can be concluded that the activity of the catalyst system increases with increasing pressure and decreases when the temperature is raised above 35° C. It can also be concluded that the activity increases with a lower amount of catalyst.

TABLE VI

| | 5 μmol Cr | | 2.5/μmol Cr |
|---|---|---|---|
| ($kg_{PE}/(mol \cdot h)$) | 15 bars | 45 bars | 45 bars |
| 25° C. | 773 | 1 722 | 3 606 |
| 35° C. | 1 016 | 1 341 | 2 790 |
| 55° C. | 619 | 806 | 1 196 |

For all polymerisations, the conditions were as follows: 1000 eq. MAO, solvent: toluene, polymerisation time 1 h.

The consumptions were also measured and the results are displayed in Table VII.

TABLE VII

| Temp. (° C.) | m PE (g) | Activity ($kg_{PE}/(mol \cdot h)$) | Consumption ($kg_{C2H4}/(mol \cdot h)$) |
|---|---|---|---|
| 35 | 7.49 | 2 996 | 2 729 |
| 25 | 10.77 | 4 308 | 5 738 |

For all polymerisations, the conditions were as follows: Cr 2.5 μmol, ligand L 5 μmol, ethylene pressure 45 bars, 1000 eq. MAO, solvent: toluene, polymerisation time 1 h.

Polymerisation of Ethylene with Supported Catalyst Systems.

The activity of the unsupported $CrCl_2$/ligand L catalyst system was evaluated in heptane. The catalyst system was not selective in polyethylene as the consumption of ethylene was larger than the amount of ethylene present in the polyethylene. The polymerisation conditions were as follows:

complexation time: 2 hours,

5 μmol of ligand with 2.5 μmol of Cr, polymerisation temperature: 25° C., polymerisation pressure: 45 bars, 1000 equ. of MAO, solvent: heptane, polymerisation time: 1 hour.

The results are displayed in Table VIII.

TABLE VIII

| m PE (g) | Activity ($kg_{PE}/(mol \cdot h)$) | Consumption ($kg_{C2H4}/(mol \cdot h)$) | Tm (° C.) |
|---|---|---|---|
| 6.77 | 2 708 | 6 768 | 137 |

Impregnation of the Catalyst on Silica/MAO.

5 μmol of complex $CrCl_2$/L were dissolved in 600 μl of toluene and then introduced in a schlenk with 100 mg of silica/MAO (50 $\mu mol_{Cr}/g_{Si}$) under stirring for a period of time of 30 minutes. The impregnated silica was filtered and washed either once with 600 μl of toluene and three times with 600 μl of heptane (condition 1) or three times with 600 μl of heptane (condition 2).

Polymerisation of Ethylene with Impregnated Silica/MAO.

The reactor was dried under nitrogen for a period of time of 30 minutes and at a temperature of 90° C. 50 mL of heptane were then introduced into the reactor with 100 mL of scavenger, MAO (30%) diluted in 5 mL of heptane, at a temperature of 25° C. 50 mg of silica, containing about 2.5 μmol of activated catalyst (50 $\mu mol_{Cr}/g_{SiO2}$) were introduced into the reactor with 5 mL of heptane. The polymerisation reaction was carried out at a temperature of 25° C. under an ethylene pressure of 45 bars and for a period of time of 1 hour for conditions 1 and 2. The results are displayed in Table IX.

TABLE IX

| | m PE (g) | Activity (kg$_{PE}$/mol · h) | Consumption (kg$_{C2H4}$/(mol · h) | Activity (g$_{PE}$/(g$_{si}$ · h)) | Consumption (g$_{C2H4}$/(g$_{si}$ · h)) | Tm (° C.) |
|---|---|---|---|---|---|---|
| Cond. 1 | ~0 | 0 | 4 836 | 0 | 242 | — |
| Cond. 2 | 0.77 | 308 | 5 061 | 15.4 | 253 | 138 |

Polymerisation of alpha-olefins.

The unsupported catalyst system CrCl$_2$/L was used for the polymerisaton of hexene with the following conditions: CrCl$_2$/L/MAO/hexene=1/100/2000. After a period of time of 24 hours and a polymerisation temperature of 30° C. the yield was of about 4.5%.

The invention claimed is:

1. A method for preparing a metallic complex comprising:
    preparing a carbonylamino fulvene ligand by condensation reaction of an hydroxycarbonyl fulvene ligand with a primary amine;

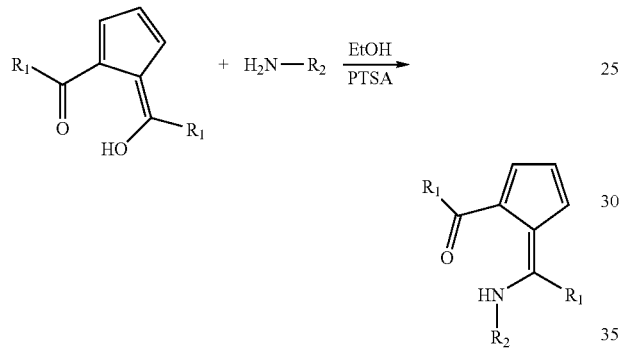

wherein R$_1$ and R$_2$ are the same or different and are selected from alkyl, aryl, alkylaryl, arylalkyl having at most 20 carbon atoms or heteroatom-containing groups;
providing a metallic precursor MZ$_n$ wherein M is a metal Group 6 to 11 of the Periodic Table, Z is a negative counter-anion and n is the valence of M;
complexing the metallic precursor with the carbonylamino fulvene; and
retrieving a metallic complex.

2. The method of claim 1, wherein R$_1$ is an alkyl, a substituted or an unsubstituted phenyl group, or CHPh$_2$, wherein phenyl group Ph is substituted or unsubstituted, or a heteroatom-containing group.

3. The method of claim 2, wherein R$_1$ is CHPh$_2$, paramethoxyphenyl or cyclohexyl.

4. The method of claim 1, wherein R$_2$ is CH$_2$pyridine or CH$_2$furan.

5. The method of claim 1, wherein R$_1$ is CHPh$_2$ and R$_2$ is CH$_2$pyridine, or wherein R$_1$ is paramethoxyphenyl and R$_2$ is CH$_2$pyridine, or wherein R$_1$ is cyclohexyl and R$_2$ is CH$_2$furan.

6. The method of claim 1, wherein M is Cr(II), Cr(III) or Ni.

7. The method of claim 1, wherein Z is halogen or acetate.

8. A metallic complex obtained by the method of claim 1.

9. An active catalyst comprising the metallic complex of claim 8, an activating agent having an ionising action and optionally a support.

10. The active catalyst system of claim 9, wherein the activating agent is methylaluminoxane.

11. A method for preparing an active catalyst system comprising:
    providing a carbonylamino fulvene ligand;
    complexing the ligand with a metallic salt MZ$_n$ in a solvent, wherein M is a metal Group 6 to 11 of the Periodic Table, Z is a negative counter-anion and n is the valence of M;
    retrieving a catalyst component;
    optionally depositing the catalyst component on a support;
    activating the catalyst component with an activating agent having an ionising action;
    optionally adding a scavenger; and
    retrieving an active oligomerisation or polymerisation catalyst system.

12. A method for oligomerising or for homo- or co-polymerising ethylene and alpha-olefins comprising:
    injecting the active catalyst system of claim 9 into a reactor;
    injecting the monomer and optional comonomer into the reactor;
    maintaining the reactor under polymerisation conditions; and
    retrieving oligomers and/or polymer.

13. The method of claim 12, wherein the monomer and comonomer are selected from ethylene, propylene or 1-hexene.

* * * * *